United States Patent [19]

Annoura et al.

[11] Patent Number: 5,723,475

[45] Date of Patent: Mar. 3, 1998

[54] ARYLPIPERIDINE AND ARYLPIPERAZINE DERIVATIVES AND MEDICAMENT CONTAINING THE SAME

[75] Inventors: Hirokazu Annoura, Nagaokakyo; Mayumi Uesugi, Ikoma-gun; Atsuko Fukunaga, Yokohama; Shigeki Tamura, Ibaraki, all of Japan

[73] Assignee: Suntory Limited, Osaka, Japan

[21] Appl. No.: 732,284

[22] PCT Filed: Feb. 28, 1996

[86] PCT No.: PCT/JP96/00469

§ 371 Date: Oct. 28, 1996

§ 102(e) Date: Oct. 28, 1996

[87] PCT Pub. No.: WO96/26924

PCT Pub. Date: Jun. 9, 1996

[30] Foreign Application Priority Data

Feb. 28, 1995 [JP] Japan .................... 7-040597

[51] Int. Cl.[6] .................. A61K 31/445; A61K 31/495; C07D 211/26; C07D 241/04

[52] U.S. Cl. .................. 514/331; 514/211; 514/230.5; 514/255; 514/253; 514/320; 514/337; 514/357; 540/552; 544/105; 544/376; 544/393; 544/394; 546/196; 546/232; 546/234; 546/281.7; 546/337; 546/338

[58] Field of Search .................. 514/211, 230.5, 514/255, 253, 320, 337, 331, 357; 540/552; 544/105, 376, 393, 394; 546/196, 232, 234, 281.7, 337, 338

[56] References Cited

U.S. PATENT DOCUMENTS 5,084,456  1/1992  Guillaumet et al. .................. 514/252

FOREIGN PATENT DOCUMENTS

| 0 191 867 | 8/1986 | European Pat. Off. . |
| 0 266 574 | 5/1988 | European Pat. Off. . |
| 0 412 899 | 2/1991 | European Pat. Off. . |
| 0 558 245 | 9/1993 | European Pat. Off. . |
| 62-187452 | 8/1987 | Japan . |
| 63-126866 | 5/1988 | Japan . |
| 1-313461 | 12/1989 | Japan . |
| 3-77867 | 4/1991 | Japan . |
| 6-9606 | 1/1994 | Japan . |
| WO86/01203 | 12/1986 | WIPO . |
| WO89/05803 | 6/1989 | WIPO . |

OTHER PUBLICATIONS

Flouzat et al, "Novel Nonopioid Non–Antiinflammatory Analgesics: 3-(Aminoalkyl)-and 3-[(4-Aryl-1-piperazinyl)alkyl]oxazolo[4,5-b]pyridin-2(3H)-ones," *Journal of Medicinal Chemistry*, vol. 36, No. 4, pp. 497–503 (1993).

Kurokawa et al, "A new Class of Calcium Antagonists. 2.[1] Synthesis and Biological Activity of 11-[[4-[4-(4-Fluorophenyl)-1-piperazinyl]butyryl]amino]-6,11-dihydrodibenzo[b,e]-thiepin Maleate and Related Compounds," *Journal of Medicinal Chemistry*, vol. 34, pp. 927–934 (1991).

Kurokawa et al, "A New Class of Calcium Antagonists. Synthesis and Biological Activity of 11-[(ω-Aminoalkanoyl)amino]-6,6a,7,8,9,10,10a,11-octahydrodibenzo[b,e]thiepin Derivatives," *Journal of Medicinal Chemistry*, vol. 34, pp. 593–599 (1991).

Beaulieu et al, "Liquid Chromatographic Method for Determination of Trazodone and Related Compounds in Drug Raw Materials," *Journal of AOAC International*, vol. 77, No. 4, pp. 857–861 (1994).

Primary Examiner—Bernard Dentz
Assistant Examiner—Garth M. Dahlen
Attorney, Agent, or Firm—Burns, Doane, Swecker & Mathis, L.L.P.

[57] ABSTRACT

The compound of the formula (I) or its salt or a medicament containing the same

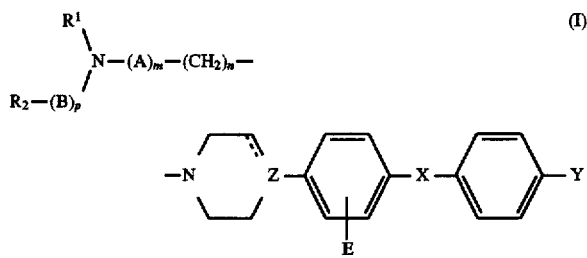

wherein, A and B represent a carbonyl group or sulfonyl group, m and p are different and represent 0 or 1, $R^1$ and $R^2$ may be the same or different from each other and represent a hydrogen atom, an unsubstituted or substituted alkyl group, an unsubstituted or substituted aryl group, an unsubstituted or substituted aralkyl group, an unsubstituted or substituted heterocyclic group containing nitrogen or an unsubstituted or substituted heterocyclic group containing oxygen, or $R^1$ and $R^2$, taken together with the nitrogen atom to which they are linked, may form an unsubstituted or substituted heterocyclic group, provided that when B is a sulfonyl group, $R^2$ does not represent a hydrogen atom, n is an integer of 1 to 6, X represents a methylene group or an oxygen atom, E and Y may be the same or different from each other and represent a hydrogen atom, a halogen atom, an alkoxy group, or an alkyl group which may be substituted by a halogen atom the dotted line shows the presence or absence of a bond, when said dotted line shows the presence of a bond, Z represents a carbon atom, and when said dotted line shows the absence of a bond, Z represents CH or a nitrogen atom.

13 Claims, No Drawings

ARYLPIPERIDINE AND ARYLPIPERAZINE DERIVATIVES AND MEDICAMENT CONTAINING THE SAME

This application is a PCT/JP 96/00469, Feb. 28, 1996.

TECHNICAL FIELD

The present invention relates to novel arylpiperidine and arylpiperazine derivatives. More specifically it relates to novel arylpiperidine and arylpiperazine derivatives useful for the medicaments having a powerful action in suppressing cytotoxic $Ca^{2+}$ overload and used for the alleviation or treatment of, for example, cerebral infarction, intracerebral hemorrhage, transient ischemic attack, subarachnoid hemorrhage, head trauma, after effects of brain surgery, after effects of cerebral arteriosclerosis, and other cerebrovascular disorders, or variant angina, unstable angina, myocardial infarction, cardiovascular system disorders accompanying surgery for revascularization by PTCA/PTCR/CABG etc., malignant arrhythmia and myocardial ischemia-reperfusion injury, and further disorders of transplanted organs at the time of organ transplants and temporary blockage of the blood flow in organs at the time of surgery, and also symptoms derived from seizures, epilepsy, migraine, etc. and pharmaceutical compositions containing these compounds are effective ingredients, medicaments for the alleviation or treatment of symptoms derived from ischemic diseases, and $Ca^{2+}$ overload suppressants.

BACKGROUND ART

In cellular disorders caused by advanced ischemia, the depletion of ATP, the fall in the pH in the cells, and the destruction of the mechanism for maintenance of the energy-dependent ion homeostasis inside and outside the cell cause the accumulation of a large amount of intracellular divalent Ca ions ($Ca^{2+}$) ($Ca^{2+}$ overload). It is believed that the $Ca^{2+}$ overload causes functional disorders in the mitochondria and randomly activates various enzyme reactions and invites further $Ca^{2+}$ overload to cause a repeated vicious cycle and in the end causes irreparable damage to the cell wall and cell death [F. B. Meyer: Brain Res. Rev., 14, 227 (1989); E. Boddeke et al.: Trends Pharmacol. Sci., 10,397 (1989)]. Therefore, drugs which suppress cytotoxic $Ca^{2+}$ overload are effective agents for the alleviation or treatment of various ischemic diseases.

Flunarizine which is used as an agent for improvement of the brain circulation [P. J. Pauwels et al.; Life Science, 48, 1881 (1991); G. E. Billman; Eur. J. Pharmacol., 212, 231 (1992)] suffers from the problem that it causes as a side effect the onset of symptoms of Parkinson's disease due to its action of blocking dopamine $D_2$ receptors. This is a major defect in its use.

DISCLOSURE OF THE INVENTION

Consequently, the objective of the present invention is to provide novel arylpiperidine and arylpiperazine derivatives, and their salts, useful as medicaments having a powerful action in suppressing cytotoxic $Ca^{2+}$ overload and used for the alleviation or treatment of ischemic diseases with no substantial side effects.

The another objective of the present invention is to provide a pharmaceutical composition, a medicament for the alleviation or treatment of ischemic diseases, and a $Ca^{2+}$ overload suppressant containing an arylpiperidine or arylpiperazine derivative or its pharmaceutically acceptable salt, as an effective ingredients.

According to the present invention, there are provided an arylpiperidine and arylpiperazine derivatives having the general formula (I):

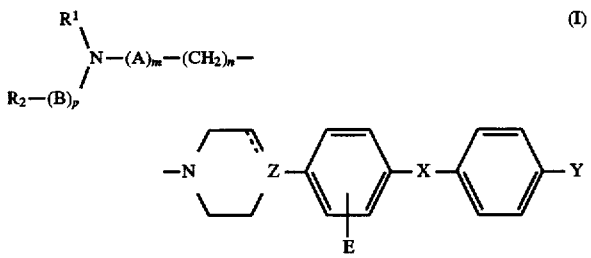

wherein, A and B represent a carbonyl group or sulfonyl group, m and p are different and represent 0 or 1, $R^1$ and $R^2$ may be the same or different from each other and represent a hydrogen atom, an unsubstituted or substituted alkyl group, an unsubstituted or substituted aryl group, an unsubstituted or substituted aralkyl group, an unsubstituted or substituted heterocyclic group containing nitrogen, an unsubstituted or substituted heterocyclic group containing oxygen or $R^1$ and $R^2$, taken together with the nitrogen atom to which they are linked, may form an unsubstituted or substituted heterocyclic group, provided that when B is a sulfonyl group, $R^2$ does not represent a hydrogen atom, n is an integer of 1 to 6, X represents a methylene group or oxygen atom, E and Y may be the same or different from each other and represent a hydrogen atom, a halogen atom, an alkoxy group, or an alkyl group which may be substituted by a halogen atom, the dotted line shows the presence or absence of a bond, when said dotted line shows the presence of a bond, Z represents a carbon atom, and when said dotted line shows the absence of a bond, Z represents CH or a nitrogen atom, and the salts thereof.

According to the present invention, there is also provided a pharmaceutical composition, a medicament for the alleviation or treatment of ischemic diseases, and a $Ca^{2+}$ overload suppressant containing an arylpiperidine or arylpiperazine derivative or its pharmaceutically acceptable salt, as an effective ingredients.

BEST MODE FOR CARRYING OUT THE INVENTION

In the present invention, ischemic diseases include cerebral ischemic diseases, for example, cerebral infarction, intracerebral hemorrhage, transient ischemic attack, subarachnoid hemorrhage, head trauma, after effects of brain surgery, after effects of cerebral arteriosclerosis, and other functional and organic diseases of the brain, ischemic heart disorders, for example, variant angina, unstable angina, myocardial infarction, cardiovascular system disorders accompanying surgery for revascularization by PTCA/PTCR/CABG etc., malignant arrhythmia and other myocardial ischemia-reperfusion injury, and also disorders of transplanted organs at the time of organ transplants, and temporary blockage of the blood flow in organs at the time of surgery.

The compounds having the general formula (I) of the present invention are concretely shown to be the following general formulas (Ia), (Ib), and (Ic).

In the general formula (Ia)

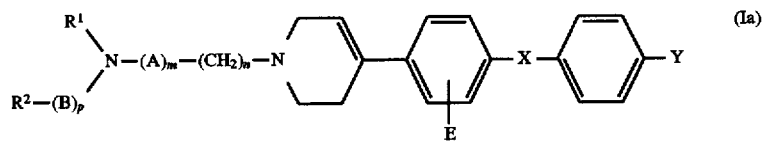

wherein, A, B, E, R¹, R², X, Y, m, n, and p are the same as defined above, examples of the unsubstituted or substituted alkyl group represented by $R^1$ or $R^2$ include preferably a $C_1$ to $C_5$ straight or branched alkyl group, more preferably an ethyl group, a propyl group, and a butyl group. These may be substituted, for example, by an amine group, a $C_1$ to $C_8$ straight or branched alkylamine group such as a methylamine group, an ethyl amine group, a dimethylamine group and a diethylamine group, a hydroxy group, a $C_1$ to $C_5$ straight or branched alkoxy group such as a methoxy group and an ethoxy group, or a $C_6$ to $C_{12}$ aryloxy group such as a phenoxy group.

Examples of the unsubstituted or substituted aryl group represented by $R^1$ or $R^2$ preferably include an unsubstituted or substituted $C_6$ to $C_{14}$ aryl group, more preferably an unsubstituted or substituted phenyl or naphthyl group. These may be substituted by, for example, a halogen atom such as a fluorine atom, a chlorine atom and a bromine atom, a hydroxy group, a $C_1$ to $C_5$ straight or branched alkoxy group such as a methoxy group and an ethoxy group, a $C_6$ to $C_{12}$ aryloxy group such as a phenoxy group, a $C_1$ to $C_5$ straight or branched alkyl group which may be substituted by a halogen atom such as a methyl group, an ethyl group and a trifluoromethyl group, or a $C_7$ to $C_{10}$ aralkyl group such as a benzyl group. More preferable examples of the unsubstituted or substituted aryl group represented by $R^1$ or $R^2$ include a 2-benzylphenyl group, a 2-benzyl-6-methylphenyl group, a 2,6-dimethylphenyl group, a 2,4,6-trimethylphenyl group, and a 1-naphthyl group.

Examples of the unsubstituted or substituted aralkyl group represented by $R^1$ or $R^2$ include preferably an unsubstituted or substituted $C_7$ to $C_{12}$ aralkyl group, more preferably an unsubstituted or substituted benzyl, phenetyl, phenylpropyl, or napthylethyl group. These may be substituted by, for example, a halogen atom such as a fluorine atom, a chlorine atom and a bromine atom, a hydroxy group, a $C_1$ to $C_5$ straight or branched alkoxy group such as a methoxy group and an ethoxy group, a $C_6$ to $C_{12}$ aryloxy group such as a phenoxy group, a $C_1$ to $C_5$ straight or branched alkyl group which may be substituted by a halogen atom such as a methyl group, an ethyl group and a trifluoromethyl group, or a methylene group. More preferable examples of the unsubstituted or substituted aralkyl group represented by $R^1$ or $R^2$ include a benzyl group, a 2-phenylethyl group, a 1-phenylvinyl group, and a trans-2-phenyl-1-cyclopropyl group.

Examples of the unsubstituted or substituted heterocyclic group containing nitrogen represented by $R^1$ or $R^2$, include preferably an unsubstituted or substituted $C_6$ to $C_{14}$ heterocyclic group containing nitrogen, more preferably an unsubstituted or substituted pyridyl, quinolyl, and acridinyl group. These may be substituted by, for example, a halogen atom such as a fluorine atom, a chlorine atom and a bromine atom, a hydroxy group, a $C_1$ to $C_5$ straight or branched alkoxy group such as a methoxy group and an ethoxy group, a $C_1$ to $C_5$ straight or branched alkyl group which may be substituted by a halogen atom such as a methyl group, an ethyl group and a trifluoromethyl group, or a $C_7$ to $C_{10}$ aralkyl group such as a benzyl group. More preferable examples of the unsubstituted or substituted heterocyclic group containing nitrogen represented by $R^1$ or $R^2$, include a 3-pyridyl group, a 3-quinolyl group, and a 9-acrydinyl group.

Examples of the unsubstituted or substituted heterocyclic group containing oxygen represented by $R^1$ or $R^2$, preferably include a chromanyl group, an isochromanyl group, and a 2,3,4,5-tetrahydro-1-benzoxepin-5-yl group. These may be substituted by, for example, a halogen atom such as a fluorine atom, a chlorine atom and a bromine atom, a hydroxy group, a $C_1$ to $C_5$ straight or branched alkoxy group such as a methoxy group and an ethoxy group, a $C_6$ to $C_{12}$ aryloxy group such as a phenoxy group, or a $C_1$ to $C_5$ straight or branched alkyl group which may be substituted by a halogen atom such as a methyl group, an ethyl group and a trifluoromethyl group. More preferable examples of the unsubstituted or substituted heterocyclic group containing oxygen represented by $R^1$ or $R^2$, include a 4-chromanyl group and a 2,3,4,5-tetrahydro-1-benzoxepin-5-yl group.

Examples of the unsubstituted or substituted heterocyclic group which the $R^1$ and $R^2$ form, taken together with the nitrogen atom to which they are linked, include preferably a 1,2,3,4-tetrahydroquinolin-1-yl group, a 1,2,3,4-tetrahydroisoquinolin-2-yl group, a 1,2,3,4-tetrahydro-5H-1-benzazepin-1-yl group, a 3,4-dihydro-2H-1,4-benzoxazin-4-yl group, a 2,3,4,5-tetrahydro-1,5-benzoxazepin-5-yl group, a 3,4-dihydro-2(1H)-quinolinon-1-yl group, a 1,2,3,4-tetrahydroisoquinolin-1-on-2-yl group, a 1,2,3,4-tetrahydroisoquinolin-3-on-2-yl group, an oxyindol-1-yl group, a 2,3,4,5-tetrahydro-1H-2-benzazepin-1-on-2-yl group, and a 2,3,4,5-tetrahydro-1,4-benzoxazepin-5-on-4-yl group. These may be substituted by, for example, a halogen atom such as a fluorine atom, a chlorine atom and a bromine atom, a hydroxy group, a $C_1$ to $C_5$ straight or branched alkoxy group such as a methoxy group and an ethoxy group, a $C_6$ to $C_{12}$ aryloxy group such as a phenoxy group, or a $C_1$ to $C_5$ straight or branched alkyl group which may be substituted by a halogen atom such as a methyl group, an ethyl group and a trifluoromethyl group. More preferable examples of these unsubstituted or substituted heterocyclic groups, include a 3,4-dihydro-2H-1,4-benzoxazin-4-yl group and a 2,3,4,5-tetrahydro-1,5-benzoxazepin-5-yl group.

In the above definition, examples of the halogen atom of the $C_1$ to $C_5$ straight or branched alkyl group which may be substituted by a halogen atom, include a fluorine atom, a chlorine atom, and a bromine atom.

n is preferably an integer of 1 to 5, more preferably an integer of 1, 3, or 5.

Examples of the halogen atom, the alkoxy group, or the alkyl group which may be substituted by a halogen atom represented by E or Y, include preferably a halogen atom such as a fluorine atom, a chlorine atom, and a bromine atom, a $C_1$ to $C_5$ straight or branched alkoxy group such as a methoxy group and an ethoxy group, a $C_1$ to $C_5$ straight or branched alkyl group which may be substituted by a halogen atom such as a methyl group, an ethyl group and a trifluoromethyl group.

Examples of the halogen atom of the alkyl group which may be substituted by a halogen atom include a fluorine atom, a chlorine atom, and a bromine atom.

In the general formula (Ib):

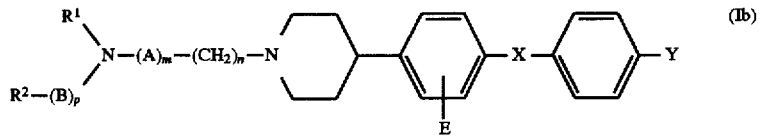

wherein, A, B, E, $R^1$, $R^2$, X, Y, m, n, and p are the same as defined above, examples of the unsubstituted or substituted alkyl group represented by $R^1$ or $R^2$, include preferably a straight or branched alkyl group, more preferably an ethyl group, a propyl group, and a butyl group. These may be substituted by, for example, an amine group, a $C_1$ to $C_8$ straight or branched alkylamine group such as a methylamine group, an ethylamine group, a dimethylamine group, and a diethylamine group, a hydroxy group, a $C_1$ to $C_5$ straight or branched alkoxy group such as a methoxy group and an ethoxy group, or a $C_6$ to $C_{12}$ aryloxy group such as a phenoxy group.

Examples of the unsubstituted or substituted aryl group represented by $R^1$ or $R^2$, include preferably an unsubstituted or substituted $C_6$ to $C_{14}$ aryl group, more preferably an unsubstituted or substituted phenyl and naphthyl group. These may be substituted by, for example, a halogen atom such as a fluorine atom, a chlorine atom and a bromine atom, a hydroxy group, a $C_1$ to $C_5$ straight or branched alkoxy group such as a methoxy group and an ethoxy group, a $C_6$ to $C_{12}$ aryloxy group such as a phenoxy group, a $C_1$ to $C_5$ straight or branched alkyl group which may be substituted by a halogen atom such as a methyl group, an ethyl group and a trifluoromethyl group, or a $C_7$ to $C_{10}$ aralkyl group such as a benzyl group. More preferable examples of the unsubstituted or substituted aryl group represented by $R^1$ or $R^2$, include a 2-benzylphenyl group, a 2-benzyl-6-methylphenyl group, a 2,6-dimethylphenyl group, a 2,4,6-trimethylphenyl group, and a 1-naphthyl group.

Examples of the unsubstituted or substituted aralkyl group represented by $R^1$ or $R^2$, include preferably an unsubstituted or substituted $C_7$ to $C_{12}$ aralkyl group, more preferably an unsubstituted or substituted benzyl, phenetyl, phenylpropyl, and napthylethyl group. These may be substituted by, for example, a halogen atom such as a fluorine atom, a chlorine atom and a bromine atom, a hydroxy group, a $C_1$ to $C_5$ straight or branched alkoxy group such as a methoxy group and an ethoxy group, a $C_6$ to $C_{12}$ aryloxy group such as a phenoxy group, a $C_1$ to $C_5$ straight or branched alkyl group which may be substituted by a halogen atom such as a methyl group, an ethyl group and a trifluoromethyl group, or a methylene group, etc. More preferable examples of the unsubstituted or substituted aralkyl group represented by $R^1$ or $R^2$, include a benzyl group, a 2-phenylethyl group, a 1-phenylvinyl group, and a trans-2-phenyl-1-cyclopropyl group.

Examples of the unsubstituted or substituted heterocyclic group containing nitrogen represented by $R^1$ or $R^2$, include preferably an unsubstituted or substituted $C_6$ to $C_{14}$ heterocyclic group containing nitrogen, more preferably an unsubstituted or substituted pyridyl, quinolyl and acridinyl group. These may be substituted by, for example, a halogen atom such as a fluorine atom, a chlorine atom and a bromine atom, a hydroxy group, a $C_1$ to $C_5$ straight or branched alkoxy group such as a methoxy group and an ethoxy group, a $C_6$ to $C_{12}$ aryloxy group such as a phenoxy group, a $C_1$ to $C_5$ straight or branched alkyl group which may be substituted by a halogen atom such as a methyl group, an ethyl group and a trifluoromethyl group, or a $C_7$ to $C_{10}$ aralkyl group such as a benzyl group. More preferable examples of the unsubstituted or substituted heterocyclic group containing nitrogen represented by $R^1$ or $R^2$, include a 3-pyridyl group, a 3-quinolyl group, and a 9-acrydinyl group.

Examples of the unsubstituted or substituted heterocyclic group containing oxygen represented by $R^1$ or $R^2$, include preferably a chromanyl group, an isochromanyl group, and a 2,3,4,5-tetrahydro-1-benzoxepin-5-yl group. These may be substituted by, for example, a halogen atom such as a fluorine atom, a chlorine atom and a bromine atom, a hydroxy group, a $C_1$ to $C_5$ straight or branched alkoxy group such as a methoxy group and an ethoxy group, a $C_6$ to $C_{12}$ aryloxy group such as a phenoxy group, or a $C_1$ to $C_5$ straight or branched alkyl group which may be substituted by a halogen atom such as a methyl group, an ethyl group and a trifluoromethyl group. More preferable examples of the unsubstituted or substituted heterocyclic group containing oxygen represented by $R^1$ or $R^2$ include a 4-chromanyl group and a 2,3,4,5-tetrahydro-1-benzoxepin-5-yl group.

Examples of the unsubstituted or substituted heterocyclic group in which the $R^1$ and $R^2$ form, taken together with the nitrogen atom to which they are linked, include preferably a 1,2,3,4-tetrahydroquinolin-1-yl group, a 1,2,3,4-tetrahydroisoquinolin-2-yl group, a 1,2,3,4-tetrahydro-5H-1-benzazepin-1-yl group, a 3,4-dihydro-2H-1,4-benzoxazin-4-yl group, a 2,3,4,5-tetrahydro-1,5-benzoxazepin-5-yl group, a 3,4-dihydro-2(1H)-quinolinon-1-yl group, a 1,2,3,4-tetrahydroisoquinolin-1-on-2-yl group, a 1,2,3,4-tetrahydroisoquinolin-3-on-2-yl-group, an oxindol-1-yl group, a 2,3,4,5-tetrahydro-1H-2-benzazepin-1-on-2-yl group, and a 2,3,4,5-tetrahydro-1,4-benzoxazepin-5-on-4-yl group. These may be substituted by, for example, a halogen atom such as a fluorine atom, a chlorine atom and a bromine atom, a hydroxy group, a $C_1$ to $C_5$ straight or branched alkoxy group such as a methoxy group and an ethoxy group, a $C_6$ to $C_{12}$ aryloxy group such as a phenoxy group, or a $C_1$ to $C_5$ straight or branched alkyl group which may be substituted by a halogen atom such as a methyl group, an ethyl group and a trifluoromethyl group. More preferable examples of these unsubstituted or substituted heterocyclic groups, include a 3,4-dihydro-2H-1,4-benzoxazin-4-yl group and a 2,3,4,5-tetrahydro-1,5-benzoxazepin-5-yl group.

In the above definition, examples of the halogen atom of the $C_1$ to $C_5$ straight or branched alkyl group which may be substituted by a halogen atom, include a fluorine atom, a chlorine atom and a bromine atom.

n is preferably an integer of 1 to 5, more preferably an integer of 1, 3, or 5.

Examples of the halogen atom, the alkoxy group, or the alkyl group which may be substituted by a halogen atom represented by E or Y, include preferably a halogen atom such as a fluorine atom, a chlorine atom and a bromine atom, a $C_1$ to $C_5$ straight or branched alkoxy group such as a methoxy group and an ethoxy group, and a $C_1$ to $C_5$ straight or branched alkyl group which may be substituted by a halogen atom such as a methyl group, an ethyl group and a trifluoromethyl group. Examples of the halogen atom of the alkyl group which may be substituted by a halogen atom, include a fluorine atom, a chlorine atom, and a bromine atom.

In the general formula (Ic):

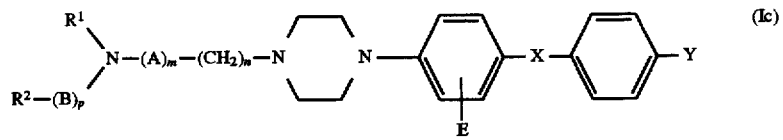

wherein, A, B, E, $R^1$, $R^2$, X, Y, m, n, and p are the same as defined above, examples of unsubstituted or substituted alkyl group represented by $R^1$ or $R^2$, include preferably a $C_1$ to $C_5$ straight or branched alkyl group, more preferably an ethyl group, a propyl group, and a butyl group. These may be substituted by, for example, an amine group, a $C_1$ to $C_8$ straight or branched alkylamine group such as a methylamine group, an ethylamine group, a dimethylamine group and a diethylamine group, a hydroxy group, a $C_1$ to $C_5$ straight or branched alkoxy group such as a methoxy group and an ethoxy group, or a $C_6$ to $C_{12}$ aryloxy group such as a phenoxy group.

Examples of the unsubstituted or substituted aryl group represented by $R^1$ or $R^2$ include preferably an unsubstituted or substituted $C_6$ to $C_{14}$ aryl group, more preferably a unsubstituted or substituted phenyl and naphthyl group. These may be substituted by, for example, a halogen atom such as a fluorine atom, a chlorine atom and a bromine atom, a hydroxy group, a $C_1$ to $C_5$ straight or branched alkoxy group such as a methoxy group and an ethoxy group, a $C_6$ to $C_{12}$ aryloxy group such as a phenoxy group, a $C_1$ to $C_5$ straight or branched alkyl group which may be substituted by a halogen atom such as a methyl group, an ethyl group and a trifluoromethyl group, or a $C_7$ to $C_{10}$ aralkyl group such as a benzyl group. More preferable examples of the unsubstituted or substituted aryl group represented by $R^1$ or $R^2$, include a 2-benzylphenyl group, a 2-benzyl-6-methylphenyl group, a 2,6-dimethylphenyl group, a 2,4,6-trimethylphenyl group, and a 1-naphthyl group.

Examples of the unsubstituted or substituted aralkyl group represented by $R^1$ or $R^2$, include preferably an unsubstituted or substituted $C_7$ to $C_{12}$ aralkyl group, more preferably an unsubstituted or substituted benzyl, phenetyl, phenylpropyl and napthylethyl group. These may be substituted by, for example, a halogen atom such as a fluorine atom, a chlorine atom and a bromine atom, a hydroxy group, a $C_1$ to $C_5$ straight or branched alkoxy group such as a methoxy group and an ethoxy group, a $C_6$ to $C_{12}$ aryloxy group such as a phenoxy group, a $C_1$ to $C_5$ straight or branched alkyl group which may be substituted by a halogen atom such as a methyl group, an ethyl group and a trifluoromethyl group, or a methylene group, etc. More preferable examples of the unsubstituted or substituted aralkyl group represented by $R^1$ or $R^2$, include a benzyl group, a 2-phenylethyl group, a 1-phenylvinyl group, and a trans-2-phenyl-1-cyclopropyl group.

Examples of the unsubstituted or substituted heterocyclic group containing nitrogen represented by $R^1$ or $R^2$, include preferably an unsubstituted or substituted $C_6$ to $C_{14}$ heterocyclic group containing nitrogen, more preferably an unsubstituted or substituted pyridyl, quinolyl and acridinyl group. These may be substituted by, for example, a halogen atom such as a fluorine atom, a chlorine atom and a bromine atom, a hydroxy group, a $C_1$ to $C_5$ straight or branched alkoxy group such as a methoxy group and an ethoxy group, a $C_6$ to $C_{12}$ aryloxy group such as a phenoxy group, a $C_1$ to $C_5$ straight or branched alkyl group which may be substituted by a halogen atom such as a methyl group, an ethyl group, and a trifluoromethyl group, or a $C_7$ to $C_{10}$ aralkyl group such as a benzyl group. More preferable examples of the unsubstituted or substituted heterocyclic group containing nitrogen represented by $R^1$ or $R^2$, include a 3-pyridyl group, a 3-quinolyl group, and a 9-acrydinyl group.

Examples of the unsubstituted or substituted heterocyclic group containing oxygen represented by $R^1$ or $R^2$, include preferably a chromanyl group, an isochromanyl group, and a 2,3,4,5-tetrahydro-1-benzoxepin-5-yl group. These may be substituted by, for example, a halogen atom such as a fluorine atom, a chlorine atom and a bromine atom, a hydroxy group, a $C_1$ to $C_5$ straight or branched alkoxy group such as a methoxy group and an ethoxy group, a $C_6$ to $C_{12}$ aryloxy group such as a phenoxy group, or a $C_1$ to $C_5$ straight or branched alkyl group which may be substituted by a halogen atom such as a methyl group, an ethyl group and a trifluoromethyl group. More preferable examples of the unsubstituted or substituted heterocyclic group containing oxygen represented by $R^1$ or $R^2$, include a 4-chromanyl group and a 2,3,4,5-tetrahydro-1-benzoxepin-5-yl group.

Examples of the unsubstituted or substituted heterocyclic group which the $R^1$ and $R^2$ form, taken together with the nitrogen atom to which they are linked, include preferably a 1,2,3,4-tetrahydroquinolin-1-yl group, a 1,2,3,4-tetrahydroisoquinolin-2-yl group, a 1,2,3,4-tetrahydro-5H-1-benzazepin-1-yl group, a 3,4-dihydro-2H-1,4-benzoxazin-4-yl group, a 2,3,4,5-tetrahydro-1,5-benzoxazepin-5-yl group, a 3,4-dihydro-2(1H)-quinolinon-1-yl group, a 1,2,3,4-tetrahydroisoquinolin-1-on-2-yl group, a 1,2,3,4-tetrahydroisoquinolin-3-on-2-yl group, an oxindol-1-yl group, a 2,3,4,5-tetrahydro-1H-2-benzazepin-1-on-2-yl group, and a 2,3,4,5-tetrahydro-1,4-benzoxazepin-5-on-4-yl group. These may be substituted by, for example, a halogen atom such as a fluorine atom, a chlorine atom and a bromine atom, a hydroxy group, a $C_1$ to $C_5$ straight or branched alkoxy group such as a methoxy group and an ethoxy group, a $C_6$ to $C_{12}$ aryloxy group such as a phenoxy group, or a $C_1$ to $C_5$ straight or branched alkyl group which may be substituted by a halogen atom such as a methyl group, an ethyl group and a trifluoromethyl group. More preferable examples of the unsubstituted or substituted heterocyclic group, include a 3,4-dihydro-2H-1,4-benzoxazin-4-yl group and a 2,3,4,5-tetrahydro-1,5-benzoxazepin-5-yl group.

In the above definition, examples of the halogen atom of the $C_1$ to $C_5$ straight or branched alkyl group which may be substituted by a halogen atom, include a fluorine atom, a chlorine atom and a bromine atom.

n is preferably an integer of 1 to 5, more preferably an integer of 1, 3, or 5.

Examples of the halogen atom, the alkoxy group, or the alkyl group which may be substituted by a halogen atom represented by E or Y, include preferably a halogen atom such as a fluorine atom, a chlorine atom and a bromine atom, a $C_1$ to $C_5$ straight or branched alkoxy group such as a methoxy group and an ethoxy group, and a $C_1$ to $C_5$ straight or branched alkyl group which may be substituted by a halogen atom such as a methyl group, an ethyl group and a trifluoromethyl group. Examples of the halogen atom of the alkyl group which may be substituted by a halogen atom, include a fluorine atom, a chlorine atom, and a bromine atom.

Preferable examples of the compounds having the general formula (I) of the present invention, include one where Z is CH or a nitrogen atom. More preferable examples include one where one of the substituent $R^1$ and $R^2$ in the general formula (I) is a hydrogen atom. In the compounds having the general formula (I), particularly preferable examples are listed as follows:

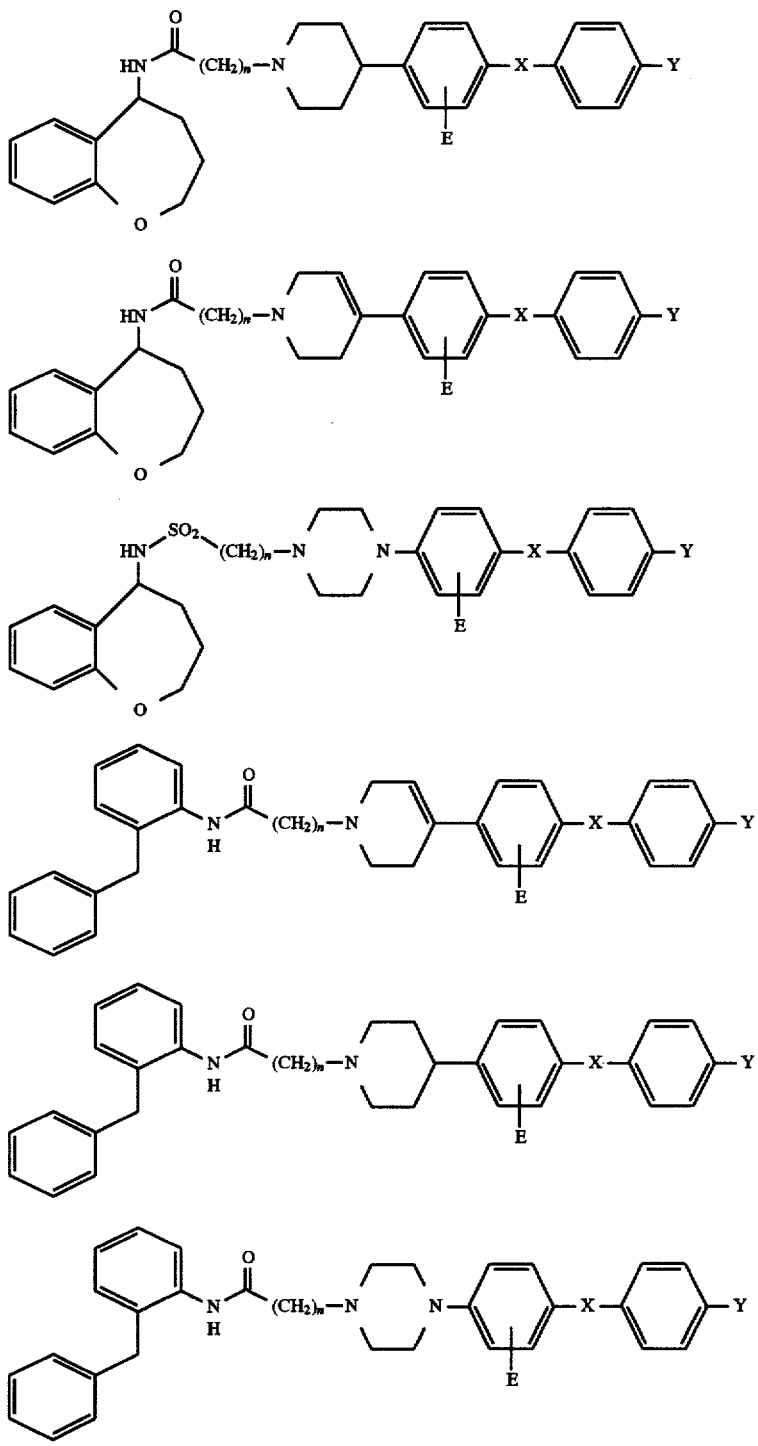

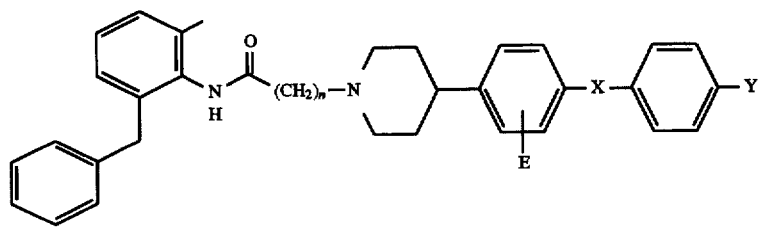
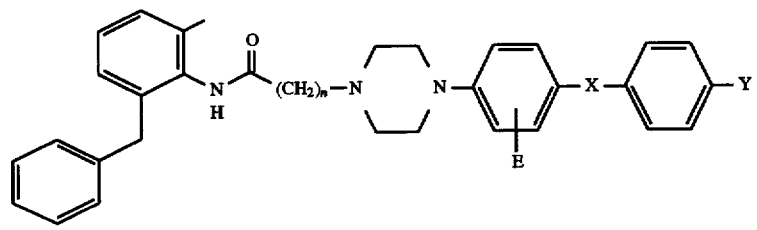
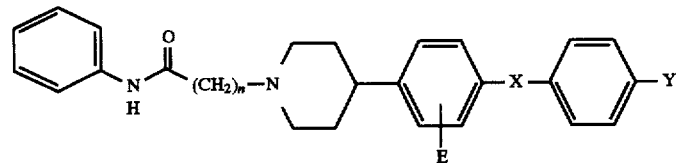
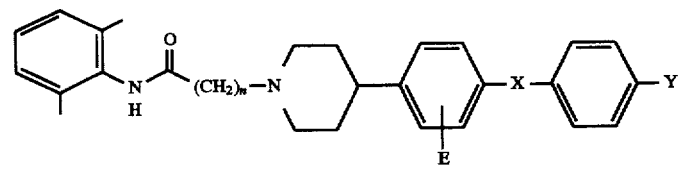
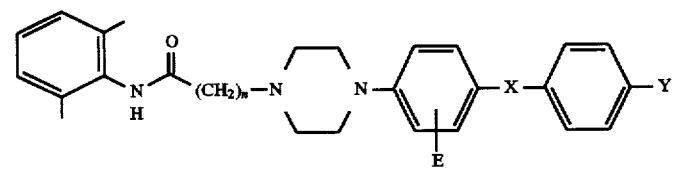
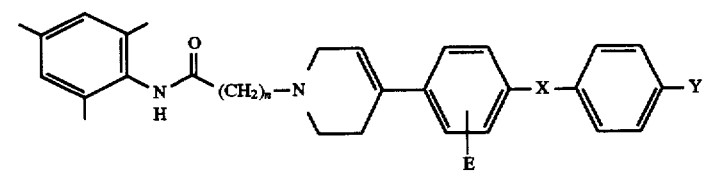
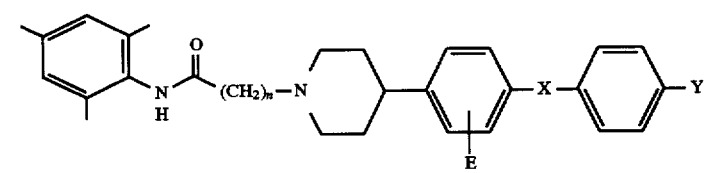
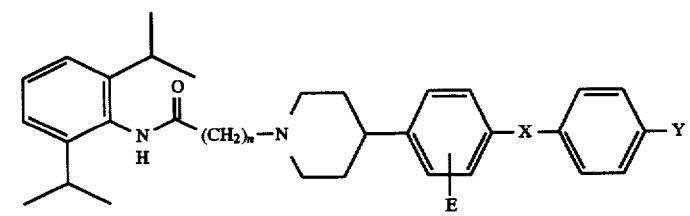

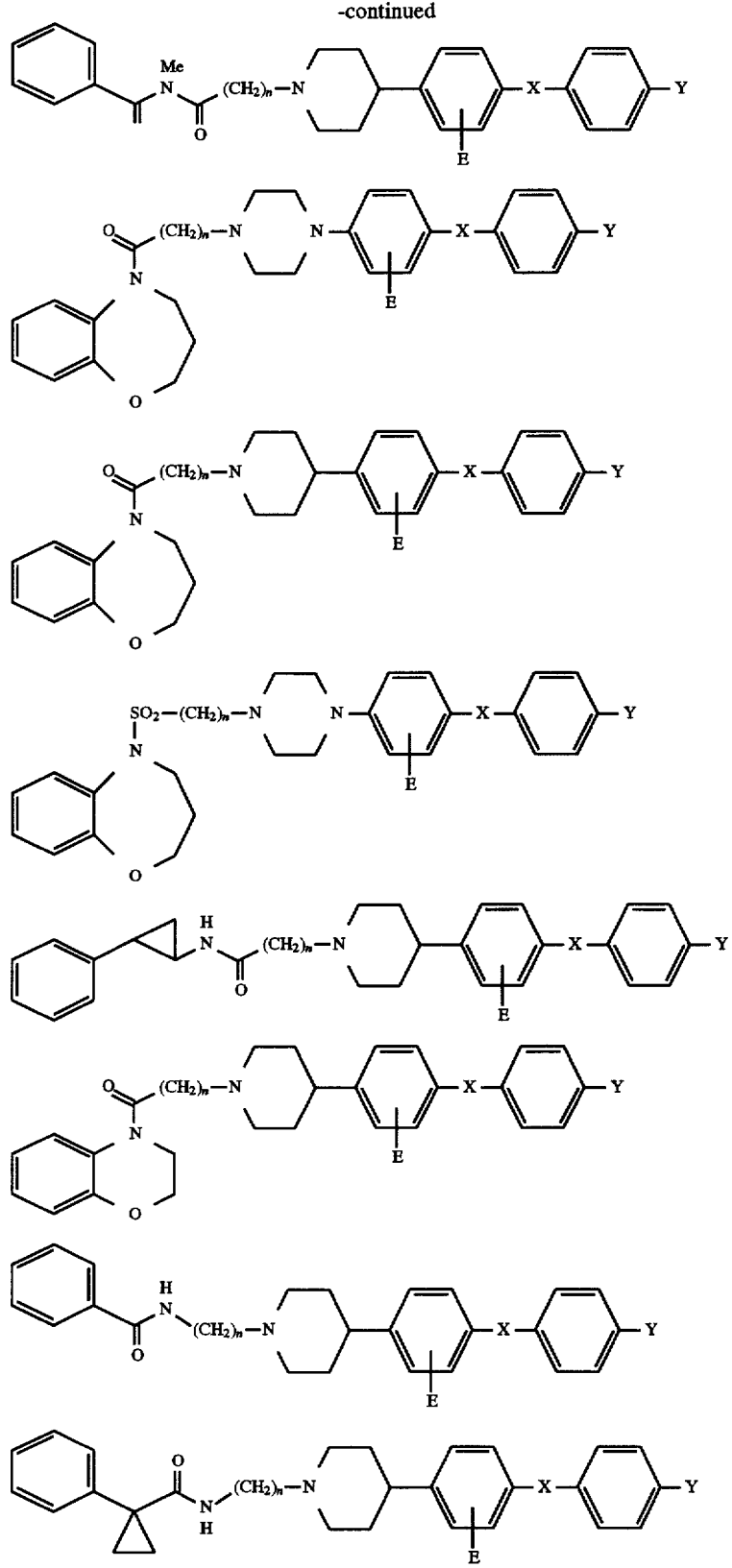
wherein, E, X, Y, and n are the same as defined above.

The compounds having the general formula (I) of the present invention include isomers, for example, optical isomers. The present invention includes all of these individual isomers and mixtures of the same.

The compounds having the general formula (I), for example, can be synthesized in the following manners. These methods will be successively explained below.

The compound (Ia) where, in the general formula (I), Z represents a carbon atom and the compound (Ib) where Z represents CH can be obtained as follows: The compound (IV) is obtained from a known starting material (II) (Step 1), then the compound (V) is obtained from the compound (IV) (Step 2). Next, the compound (VII) is made to react with the compound (VI) to obtain the compound (VIII) (Step 3), which is then made to react with the compound (IV) to obtain the compound (Ia) (Step 4). The compound (Ib) can be obtained similarly from the compound (VIII) and the compound (V) (Step 5).

When in the general formulas (Ia) and (Ib) B represents a carbonyl group or sulfonyl group, $R^1$ represents a hydrogen atom, and p=1 and m=0, the compound (Ia') may be obtained from the compound (IV) (Step 6) and the compound (Ib') may be obtained from the compound (V) (Step 7).

The compound (Ic) where, in the general formula (I), Z represents a nitrogen atom may be obtained from the known starting material (XIII) (Step 8).

Step 1:
The compound (IV) can be synthesized from the known starting material (II) by the following method:

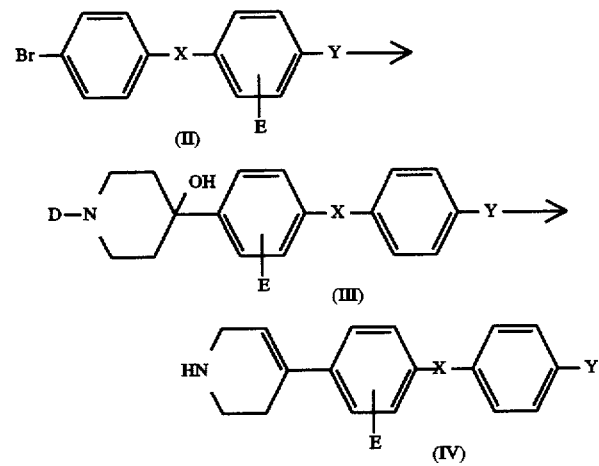

wherein, E, X, and Y are the same as defined above, and D represents a tert-butoxycarbonyl group, an ethoxycarbonyl group, or an acetyl group.

That is, an aryl bromide derivative having the general formula (II) is converted by the conventional method to the corresponding aryl Grignard reagent or aryl lithium reagent, then is reacted in tetrahydrofuran, diethylether, ethyleneglycol dimethylether, toluene, or another solvent, which is not participating in the reaction, at −100° to 50° C., preferably −78° C. to room temperature, with 1 to 1.5 equivalents of known starting material N-tert-butoxycarbonyl-4-piperidone, N-ethoxycarbonyl-4-piperidone, or N-acetyl-4-piperidone for 1 to 6 hours so as to obtain the compound having the general formula (III).

The starting material (II) used in the reaction is a known compound as described by Martin et al, [L. Martin et al.; J. Mad. Chem., 22, 1347 (1979)] or can be synthesized by the similar method. For example, 4'-bromodiphenylether, 4-bromophenylether, 4-bromo-4'-chlorodiphenylmethane, 4-bromo-4'-methoxydiphenylmethane, 4-bromo-4'-fluorodiphenylmethane, 4-bromo-4'-trifluorodiphenylmethane, 4-bromo-4'-fluoro-2-methyldiphenylmethane, 4-bromo-4'-chloro-2-methyldiphenylmethane, 4-bromo-4'-methoxy-2-methyldiphenylmethane, 4-bromo-2-methyl-4'-trifluoromethyldiphenylmethane, 4-bromo-4'-fluoro-3-methyldiphenylmethane, 4-bromo-4'-chloro-3-methyldiphenylmethane, 4-bromo-4'-methoxy-3-methyldiphenylmethane, 4-bromo-3-methyl-4'-trifluoromethyldiphenylmethane, and the like may be used.

Further, as the conditions for preparing the Grignard reagent and the organolithium reagent, the various methods described in the "Compendium for Organic Synthesis" (Wiley-Interscience: A Division of John Wiley & Sons Ltd.) etc. may be used.

The compounds obtained from the reactions may be used as they are for the next step, but if necessary may be used after purification by a generally used purification method such as recrystallization or column chromatography.

Next, the compound (III) obtained is treated under non-solvent conditions or in tetrahydrofuran, diethylether, ethyleneglycol dimethylether, benzene, toluene, methylene chloride, chloroform, carbon tetrachloride, water, methanol, ethanol, or another solvent, which is not participating in the reaction, at −20° to 150° C., preferably 0° to 80° C., with 1 to 20 equivalents of organic acids such as acetic acid, trifluoroacetic acid, methanesulfonic acid, trifluoromethanesulfonic acid, and the like or inorganic acids such as hydrochloric acid, sulfuric acid, nitric acid, and the like for 1 to 12 hours, or the compound (III) is let to react in benzene, toluene, methylene chloride, chloroform, carbon tetrachloride, or another solvent, which is not participating in the reaction, if necessary in the presence of triethylamine, pyridine, diisopropylethylamine, or other bases, at −20° to 150° C., preferably 0° to 100° C., with 1 to 5 equivalents of thionylchloride, methane sulfonylchloride, trifluoromethane sulfonylchloride, trifluoromethanesulfonic acid anhydride, p-toluene sulfonylchloride, phosphorus oxychloride, or other acid chloride derivatives for 1 to 6 hours, then performing an acid treatment similar to the above, so as to obtain a compound having the general formula (IV).

Step 2:
The compound (IV) obtained in Step 1 can be reduced to synthesize the compound (IV):

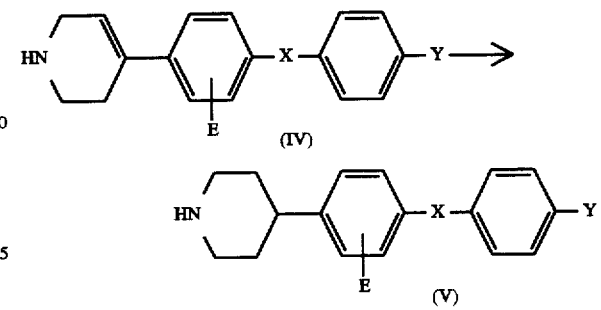

wherein, E, X, and Y are the same as defined above.

That is, the compound (IV) obtained in Step 1 can be hydrogenated in the presence of palladium carbon, platinum, or another catalyst in methanol, ethanol, ethyl acetate, or another solvent, which is not participating in the reaction at room temperature so as to convert it to the compound of the general formula (V). Further, in the present reaction, if necessary, acetic acid, hydrochloric acid, or another acid may be added.

Step 3:

The compound (VI) can be reacted with the compound (VII) to synthesize the compound (VIII).

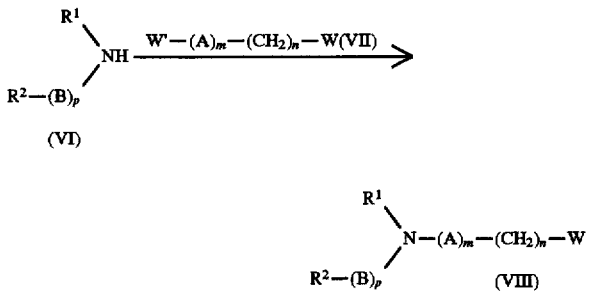

wherein, A, B, R¹, R², m, n, and p are the same as defined above, and W and W' represent groups capable of easily reacting with an amine group etc.

That is, the compound (VI) can be reacted in benzene, toluene, methylene chloride, chloroform, carbon tetrachloride, tetrahydrofuran, ether, dimethylformamide, dimethylsulfoxide, or another solvent, which is not participating in the reaction in the presence of, if necessary, organic bases such as triethylamine, pyridine and diisopropylethylamine, or inorganic bases such as sodium carbonate, potassium carbonate, sodium hydrogencarbonate, potassium hydrogencarbonate, sodium hydride and potassium tert-butoxide, at −50° to 80° C., preferably −20° C. to room temperature, with 1 to 1.5 equivalents of the compound (VII) to obtain the compound having the general formula (VIII).

W and W' are leaving groups capable of being easily reacted with an amine group and, for example, are halogen atom such as a chlorine atom and a bromine atom, an alkylsulfonyloxy group such as a methane sulfonyloxy group, or an arylsulfonyloxy group such as a p-toluene sulfonyloxy group.

As the compound (VI) to be used in the present reaction, a commercially available or known compound may be used, for example, methylamine, ethylamine, propylamine, butylamine, amylamine, isopropylamine, 3-dimethylaminopropylamine, sec-butylamine, N,N,N'-trimethylethylenediamine, aniline, N-allylaniline, N-methylaniline, o-toluidine, m-toluidine, p-toluidine, 2-fluoroaniline, 3-fluoroaniline, 4-fluoroaniline, o-anisidine, m-anisidine, p-anisidine, 2-aminobenzotrifluoride, 3-aminobenzotrifluoride, 4-aminobenzotrifluoride, 4-cyclohexylaniline, 2,3-dimethylaniline, 2,6-dimethylaniline, 2,6-diisopropylaniline, 2,6-difluoroaniline, 3-fluoro-2-methylaniline, 3-fluoro-o-anisidine, 2,3-dihydro-2,2-dimethyl-7-benzofuranamine, 3,4-(methylenedioxy) aniline, 2,4,6-trimethylaniline, 1,4-benzodioxan-6-amine, 2-phenoxyaniline, 3-phenoxyaniline, 4-phenoxyaniline, 1-aminonaphthalene, 2-aminonaphthalene, N-ethyl-1-naphthylamine, benzylamine, α-methylbenzylamine, (R)-(+)-α-methylbenzylamine, (S)-(−)-α-methylbenzylamine, phenetylamine, 2,2-diphenylethylamine, 3-phenylpropylamine, 3,3-diphenylpropylamine, 4-phenylbutylamine, 1-methyl-2-phenoxyethylamine, 1-aminoindane, 2-aminoindane, 1,2,3,4-tetrahydro-1-naphthylamine, 2-fluorobenzylamine, 4-chlorobenzhydrylamine, 1-naphthalenemethylamine, 1-(1-naphthyl)ethylamine, (R)-(+)-1-(1-naphthyl) ethylamine, (S)-(−)-1-(1-naphthyl)ethylamine, 2-benzylaniline, 2-benzyl-6-methylaniline, 5-amino-2,3,4, 5-tetrahydro-1-benzoxepine, 2,3,4,5-tetrahydro-1,5-benzoxazepine, 3,4-dihydro-2H-1,4-benzoxadine, trans-2-phenyl-1-cyclopropylamine, N-methyl-N-(1-phenylvinyl) amine, 2-aminopyridine, 3-aminopyridine, 4-aminopyridine, 4-(aminomethyl)pyridine, 3-aminoquinoline, 5-aminoquinoline, 6-aminoquinoline, 8-aminoquinoline, 9-aminoacrylidine, 5-aminoisoquinoline, benzamide, 4-fluorobenzamide, 4-methoxybenzamide, 4-(trifluoromethyl)benzamide, 2,6-difluorobenzamide, 1-phenyl-1-cyclopropanecarboxamide, benzenesulfonamide, p-toluenesulfonamide, 1,2,3,4-tetrahydroguinoline, 1,2,3,4-tetrahydroisoquinoline, 3,4-dihydro-2(1H)-quinolinone, 1,2,3,4-tetrahydroisoquinolin-1-one, 1,2,3,4-tetrahydroisoquinolin-3-one, oxyindole, 2,3, 4,5-tetrahydro-1H-2-benzazepin-1-one, 2,3,4,5-tetrahydro-1,4-benzoxazepin-5-one, 1,2,3,4-tetrahydro-5H-1-benzazepine, 3,4-dihydro-2H-1,4-benzoxadine, etc. may be used.

As the compound (VII) to be used in the present reaction, a commercially available or known compound may be used, for example, bromoacetyl bromide, bromoacetyl chloride, chloroacetyl chloride, 4-bromobutyryl bromide, 4-bromobutyryl chloride, 4-chlorobutyryl choride, 5-chlorovaleryl chloride, 5-bromovaleryl chloride, 6-bromohexanoyl chloride, 3-chloropropanesulfonyl chloride, 1,2-dibromoethane, 1,3-dibromopropane, 1,4-dibromobutane, 1,5-dibromopentane, 1,6-dibromo-n-hexane, 1-bromo-5-chloropentane, 1-bromo-3-chloropropane, 1-bromo-4-chlorobutane, 1,4-dimethanesulfonyloxybutane, 1,4-di(p-toluenesulfonyloxy) butane, etc. may be used.

Step 4:

The compound (VIII) obtained in Step 3 can be reacted with the compound (IV) obtained in Step 1 to synthesize the compound (Ia) where, in the general formula (I), Z represents a carbon atom.

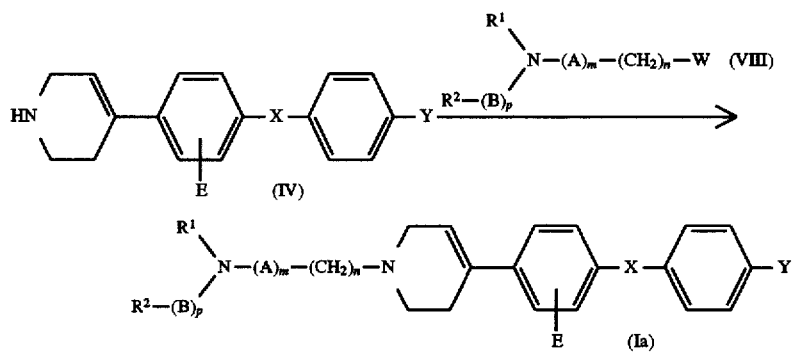

wherein, A, B, E, R¹, R², W, X, Y, m, n, and p are the same as defined above.

That is, the compound (IV) obtained in Step 1 is heated with stirring in benzene, toluene, tetrahydrofuran, dioxane, dimethylformamide, dimethylsulfoxide, acetonitrile, acetone, or another solvent, which is not participating in the reaction, in the presence of organic bases such as triethylamine, diisopropylethylamine, pyridine, and the like or inorganic bases such as sodium carbonate, potassium carbonate, cesium carbonate, cesium fluoride, sodium hydrogencarbonate, potassium hydrogencarbonate, and the like, at room temperature to 150° C., preferably room temperature to 100° C., with 0.9 to 1.2 equivalents of the compound (VIII) to obtain the tetrahydropyridine derivative having the general formula (Ia). Further, in this reaction, if necessary, sodium iodide or tetrabutylammonium iodide may be added.

Step 5:

The compound (VIII) obtained in Step 3 can be reacted with the compound (V) obtained in Step 2 by the same procedure shown in Step 4 to synthesize the compound (Ib) where, in the general formula (I), Z represents CH.

Step 6:

The compound (Ia') where, in the general formula (Ia), B represents a carbonyl or sulfonyl group, R¹ represents a hydrogen atom, p=1, and m=0 can be synthesized from the compound (IV) obtained in Step 1.

wherein, A, B, E, R¹, R², W, X, m, and p are the same as defined above.

wherein, B, E, R², W, W', X, Y, and n are as defined above.

That is, the compound (IV) obtained in Step 1 is heated with stirring in benzene, toluene, tetrahydrofuran, dioxane, dimethylformamide, dimethylsulfoxide, acetonitrile, acetone, or another solvent, which is not participating in the reaction, in the presence of organic bases such as triethylamine, diisopropylethylamine and pyridine, or inorganic bases such as sodium carbonate, potassium carbonate, cesium carbonate, cesium fluoride, sodium hydrogencarbonate and potassium hydrogencarbonate, at room temperature to 150° C., preferably room temperature to 100° C., with 0.9 to 1.2 equivalents of the compound (IX) to obtain the nitrile derivative having the general formula (X). Further, in this reaction, if necessary, sodium iodide or tetrabutylammonium iodide may be added.

As the compound (IX) to be used in this reaction, a commercially available or known compound may be used, for example, chloroacetonitrile, bromoacetonitrile, iodoacetonitrile, 3-chloropropionitrile, 3-bromopropionitrile, 4-chlorobutyronitrile, 4-bromobutyronitrile, 5-chlorovaleronitrile, 5-bromovaleronitrile, etc. may be used.

Next, the obtained compound (X) is reduced in tetrahydrofuran, diethyl ether, ethylene glycol dimethyl ether, or another solvent, which is not participating in the reaction, at −100° to 80° C., preferably −78° C. to room temperature, by 1 to 5 equivalents of lithium aluminum hydride, sodium his (2-methoxyethoxy) aluminum hydride, borane, etc. for 1 to 12 hours to obtain the diamine derivative having the general formula (XI).

Further, the obtained compound (XI) is reacted in benzene, toluene, methylene chloride, chloroform, carbon 4-fluorobenzoyl chloride, 1-phenyl-1-cyclopropanecarbonyl chloride, trans-2-phenyl-1-cyclopropanecarbonyl chloride, phenylacetyl chloride, o-toluoyl chloride, m-toluoyl chloride, p-toluoyl chloride, 4-(trifluoromethyl)benzoyl chloride, p-anisoyl chloride, 1-naphthoyl chloride, 2-naphthoyl chloride, etc. may be used.

Step 7:

By the same method as in Step 6, the compound (Ib') where, in the general formula (Ib), B represents a carbonyl or sulfonyl group, R¹ represents a hydrogen atom, p=1, and m=0, can be synthesized from the compound (V') obtained in Step 2.

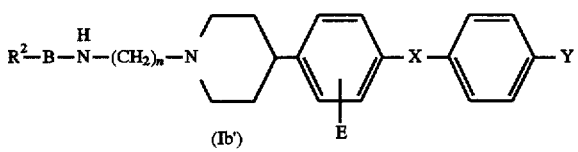

Step 8:

The compound (Ic) where, in the general formula (I), Z represents a nitrogen atom, can be synthesized from the known starting material of the compound (XIII).

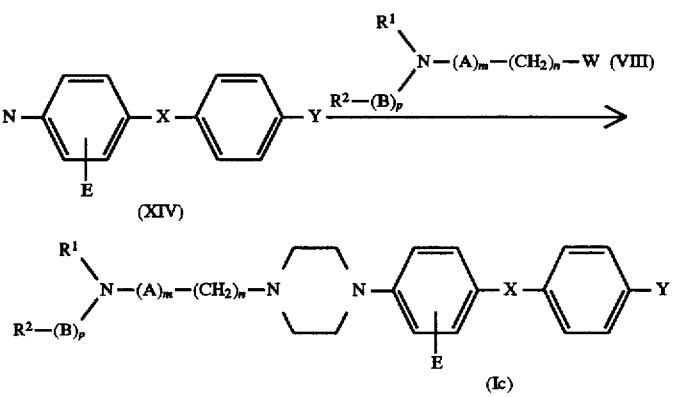

tetrachloride, or another solvent, which is not participating in the reaction, in the presence, if necessary, of organic bases such as triethylamine, pyridine and diisopropylamine, or inorganic bases such as sodium carbonate, potassium carbonate, sodium hydrogencarbonate and potassium hydrogencarbonate, at −50° to 80° C., preferably −20° C. to room temperature, with 1 to 1.5 equivalents of the compound (XII) to obtain the compound having the general formula (Ia').

As the compound (XII) to be used in this reaction, a commercially available or known compound may be used, for example, methanesulfonyl chloride, ethanesulfonyl chloride, 1-propanesulfonyl chloride, isopropylsulfonyl chloride, 1-butanesulfonyl chloride, acetyl chloride, butyryl chloride, isovaleryl chloride, tert-butylacetyl chloride, methoxyacetyl chloride, benzenesulfonyl chloride, α-toluenesulfonyl chloride, p-toluenesulfonyl chloride, 4-methoxybenzenesulfonyl chloride, 1-naphthalenesulfonyl chloride, 2-naphthalenesulfonyl chloride, benzoyl chloride, wherein, A, B, E, R¹, R², W, X, Y, m, n, and p are the same as defined above.

That is, the aniline derivative having the general formula (XII) is reacted under non-solvent conditions or in n-butanol, tert-butyl alcohol, or another solvent, which is not participating in the reaction, at 80° to 300° C., preferably 150° to 250° C., with 1 to 1.5 equivalents of the known bis-2-chloroethylamine hydrochloride for 1 to 12 hours to obtain the compound having the general formula (XIV).

The starting material (XIII) to be used in this reaction may be a commercially available or known compound described in the literature [K. Suzuki et al.: J. Org. Chem., 26, 2239 (1961)] or may be synthesized by a known method as described, for example, in Japanese Examined Patent Publication (Kokoku) No. 6-25191. For example, 4-phenoxyaniline, 4-benzylaniline, 4-(4-fluorophenyl)methylaniline, 4-(4-methoxyphenyl)methylaniline, 4-(4-chlorophenyl)methylaniline, 4-(4-trifluoromethylphenyl)methyl-aniline, 4-benzyl-3-methoxyaniline, 4-(4- fluorophenyl) methyl-3-methoxyaniline, 3-fluoro-4-(4-fluorophenyl) methylaniline, 3-fluoro-4-(4-methoxyphenyl) methylaniline, 3-methoxy-4-(4-methoxyphenyl) methylaniline, etc. may be used.

Further, in this reaction, if necessary, sodium hydrogencarbonate, potassium hydrogencarbonate, sodium carbonate, potassium carbonate, or another inorganic base may be added.

The compound (XIV) obtained in the aforementioned reaction may be used as it is in the next step, but may also be used after purification if necessary by a generally used purification method such as recrystallization or column chromatography etc.

By treating the resultant compound (XIV) by the same method as in Step 4 or Step 6, it can be converted to the arylpiperazine derivative of the general formula (Ic).

The isomers included in the compound having the general formula (I) of the present invention may be separated by conventional methods, for example, recrystallization, column chromatography, thin layer chromatography and high pressure liquid chromatography, or similar methods using optically active reagents.

The compound having general formula (I) of the present invention may be dissolved in a suitable organic solvent, for example, ether, tetrahydrofuran, methylene chloride, chloroform, benzene, toluene, etc. and treated with an inorganic or organic acid to obtain the corresponding salt. Examples of the inorganic acid to be used here include hydrochloric acid, sulfuric acid, nitric acid, phosphoric acid, periodic acid, and the like, and examples of the organic acid include formic acid, acetic acid, butyric acid, oxalic acid, malonic acid, propionic acid, valeric acid, succinic acid, fumaric acid, maleic acid, tartaric acid, citric acid, malic acid, benzoic acid, p-toluenesulfonic acid, methanesulfonic acid, and the like.

The compounds of the present invention are low in toxicity. For example, the 50% lethal dosage $LD_{50}$ of acute toxicity of the compound of compound No. 53, calculated from the death rate up to 24 hours after intravenous injection of the drug into ddY mice (male, 6 weeks old) by a conventional method, was 46.5 mg/kg.

The compounds having the general formula (I) of the present invention are low in toxicity and can be used alone by themselves or, if desired, can be prepared with other normal pharmaceutically allowable known and generally used carriers into preparations designed for the alleviation and treatment of symptoms due to ischemic diseases. For example, the effective ingredient can be administered orally or nonorally by itself or made into a capsule, tablet, injection, or other suitable preparation together with usually used excipients. For example, capsule preparations are prepared by mixing the powder with lactose, starch or its derivatives, cellulose derivatives or other excipients and packing the mixture into gelatin capsules. Further, tablets can be prepared by adding and kneading in, in addition to said excipient, a binder such as sodium carboxymethylcellulose, alginic acid and arabia gum, and water, if necessary granulating the same, then further adding talc, stearic acid, and other lubricants and preparing the final form using a usual compression tablet-making machine. At the time of non-oral administration using injection, the effective ingredient is dissolved together with a solubilizer in sterilized distilled water or sterilized physiological saline and sealed in an ampule to make the injection preparation. If necessary, a stabilizing agent, buffer, etc. may also be included.

The dosage of the pharmaceutical composition, medicament for alleviation or treatment of ischemic diseases, or $Ca^{2+}$ overload suppressant depends on various factors, for example, the symptoms and age of the patient to be treated, the route of administration, the form of the preparation, the frequency of administration, etc., but usually is 0.1 to 1000 mg/day/person, preferably 1 to 500 mg/day/person.

EXAMPLES

The present invention will now be explained in further detail with reference to the follows Reference Examples and Examples, but the present invention is of course not limited in scope to these Examples.

Reference Example 1

Synthesis of N-tert-butoxycarbonyl-4-(4-phenoxyphenyl)-4-piperidinol (1) (Note: Compound No. 1 in Table 1 (same below))

To a 100 ml of a tetrahydrofuran solution of 3.5 g of N-tert-butoxycarbonyl-4-piperidone was added dropwise, under ice cooling, 35 ml of 4-phenoxyphenyl magnesium bromide (0.6 mol/l tetrahydrofuran solution) prepared from 4-bromodiphenylether. This was stirred for 1 hour. To the reaction mixture was then added 30 ml of a saturated aqueous solution of ammonium chloride, then extraction was performed with ether. The extract was washed with saturated saline, dried, filtered, then concentrated under reduced pressure to obtain a residue which was purified by silica gel column chromatography (hexane:ethyl acetate= 3:1) to obtain the above-referenced compound (1) in an amount of 2.92 g (yield of 45%).

Reference Example 2

Synthesis of N-tert-butoxycarbonyl-4-[4-(4-fluorophenyl)methylphenyl]-4-piperidinol (2)

To a 25 ml ether solution of 2.5 g of 4-bromo-4'-fluorodiphenylmethane was gradually added dropwise at −78° C. 6.5 ml of n-butyllithium (1.6 mol/l hexane solution). This was warmed up to −20° C. and stirred for 1 hour, then an 8 ml tetrahydrofuran solution of 1.8 g of N-tert-butoxycarbonyl-4-piperidone was added dropwise. This was stirred at 0° C. for 1 hour, then 15 ml of a saturated aqueous solution of ammonium chloride was added and extraction was performed with ether. The extract was washed with saturated saline, dried, filtered, then concentrated under reduced pressure to obtain a residue which was purified by silica gel column chromatography (hexane:ethyl acetate= 4:1) to obtain the above-referenced compound (2) in an amount of 2.69 g (yield of 77%).

Reference Example 3

Synthesis of 4-(4-phenoxyphenyl)-1,2,3,6-tetrahydropyridine (3)

To a 3 ml methylene chloride solution of 772 mg of the compound (1) synthesized in Reference Example 1 was added dropwise, under ice cooling, 3 ml of trifluoroacetic acid. This was stirred at room temperature for 2 hours, then was adjusted by a 10% aqueous solution of sodium hydroxide to pH=9 to 10. Extraction was performed by ether. The extract was dried, filtered, then concentrated under reduced pressure to obtain a crude crystal which was then recrystallized by ether/methylene chloride to obtain the above-referenced compound (3) in an amount of 250 mg (yield of 47%).

Reference Example 4

Synthesis of 4-(4-phenoxyphenyl)piperidine (4)

To a 100 ml methanol solution of 3.51 g of the compound (3) synthesized in Reference Example 3 were added 200 mg of palladium carbon and 1 ml of acetic acid for hydrogenation at atmospheric pressure and room temperature. After the end of the reaction, the insolubles were filtered off and the filtrate was concentrated under reduced pressure. The obtained residue was dissolved in methylene chloride, then adjusted by a 10% aqueous solution of sodium hydroxide to pH=9 to 10, then was shaken. The organic layer was dried, filtered, then concentrated under reduced pressure to obtain a residue which was then purified by silica gel column chromatography (methylene chloride:methanol=20:1]) to obtain the above-reference compound (4) in all amount of 2.32 g (yield of 66%).

Reference Example 5

Synthesis of 1-[4-(4-fluorophenyl)methylphenyl] piperazine (5)

A mixture of 500 mg of 4-(4-fluorophenyl) methylaniline and 445 mg of bis(2-chloroethyl)amine hydrochloride was stirred at 100° C. for 2 hours, then gradually raised in temperature to 200° C. and then further stirred for 2 hours. This was then cooled to room temperature, then the product was purified by silica gel column chromatography (chloroform:methanol:water (2% acetic acid)=65:35:5) to obtain the above-referenced compound (5) in an amount of 503 mg (yield of 75%).

Reference Example 6

Synthesis of 4-[4-(4-fluorophenyl)methylphenyl]-1, 2,3,6-tetrahydropyridine (6)

The compound (2) synthesized in Reference Example 2 was used to produce the above compound in the same way as Reference Example 3.

Reference Example 7

Synthesis of 4-[4-(4-fluorophenyl)methylphenyl] piperidine (7)

The compound (6) synthesized in Reference Example 6 was used to produce the above compound in the same way as Reference Example 4.

Reference Example 8

Synthesis of 5-(2-bromoacetylamino)-2,3,4,5-tetrahydro-1-benzoxepine (8)

To a 5 ml methylene chloride solution of 150 mg of 5-amino-2,3,4,5-tetrahydro-1-benzoxepine (Japanese Unexamined Patent Publication (Kokai) No. 4-178381) and 0.15 ml of triethylamine was added dropwise, under ice cooling, 0.08 ml of bromoacetyl bromide. This was then stirred at room temperature for 1 hour. To the reaction was added 5 ml of a saturated aqueous solution of ammonium chloride, then extraction was performed with methylene chloride. The extract was washed with saturated saline, dried, filtered, then concentrated under reduced pressure to obtain a residue which was then purified by silica gel column chromatography (methylene chloride:methanol=25:1) to obtain the above-referenced compound (8) in an amount of 165 mg (yield of 65%).

Reference Example 9

Synthesis of 5-(4-chlorobutyrylamino)-2,3,4,5-tetrahydro-1-benzoxepine (9)

5-amino-2,3,4,5-tetrahydro-1-benzoxepine and 4-chlorobutyryl choride were used to produce the above compound in the same way as Reference Example 8.

Reference Example 10

Synthesis of 5-(3-chloropropylsulfamoyl)-2,3,4,5-tetrahydro-1-benzoxepine (10)

5-amino-2,3,4,5-tetrahydro-1-benzoxepine and 3-chloropropanesulfonyl chloride were used to produce the above compound in the same way as Reference Example 8.

Reference Example 11

Synthesis of 2-benzyl-1-(4-bromobutyrylamino) benzene (11)

2-benzylaniline and 4-bromobutyryl chloride were used to produce the above compound in the same way as Reference Example 8.

Reference Example 12

Synthesis of 2-benzyl-1-(6-bromohexanoylamino) benzene (12)

2-benzylaniline and 6-bromohexanoyl chloride were used to produce the above compound in the same way as Reference Example 8.

Reference Example 13

Synthesis of 2-benzyl-1-(2-bromoacetylamino)-6-methylbenzene (13)

2-benzyl-6-methylaniline [A. W. H. Wardrop et al.: J. Chem. Soc., Perkin Trans. 1, 12, 1279 (1976)] and bromoacetyl bromide were used to produce the above compound in the same way as Reference Example 8.

Reference Example 14

Synthesis of 2-benzyl-1-(4-chlorobutyrylamino)-6-methylbenzene (14)

2-benzyl-6-methylaniline and 4-chlorobutyryl choride were used to produce the above compound in the same way as Reference Example 8.

Reference Example 15

Synthesis of 5-(2-bromoacetyl)-2,3,4,5-tetrahydro-1, 5-benzoxazepine (15)

2,3,4,5-tetrahydro-1,5-benzoxazepine [E. K. Orlova et al.; Kim. Geterotsikl. Soedin.,9, 1296 (1975): Chem. abstra., 84, 59411] and bromoacetyl bromide were used to produce the above compound in the same way as Reference Example 8.

Reference Example 16

Synthesis of 5-(4-chlorobutyryl)-2,3,4,5-tetrahydro-1,5-benzoxazepine (16)

2,3,4,5-tetrahydro-1,5-benzoxazepine and 4-chlorobutyryl chloride were used to produce the above compound in the same way as Reference Example 8.

Reference Example 17

Synthesis of 5-(3-chloropropylsulfonyl)-2,3,4,5-tetrahydro-1,5-benzoxazepine (17)

2,3,4,5-tetrahydro-1,5-benzoxazepine and 3-chloropropanesulfonyl chloride were used to produce the above compound in the same way as Reference Example 8.

Reference Example 18

Synthesis of N-(2,6-dimethylphenyl)-2-bromoacetamide (18)

2,6-dimethylaniline and bromoacetyl bromide were used to produce the above compound in the same way as Reference Example 8.

Reference Example 19

Synthesis of N-(2,6-dimethylphenyl)-4-bromobutylamide (19)

2,6-dimethylaniline and 4-bromobutyryl bromide were used to produce the above compound in the same way as Reference Example 8.

Reference Example 20

Synthesis of N-(trans-2-phenyl-1-cyclopropyl)carbamoylmethyl bromide (20)

Trans-2-phenyl-1-cyclopropylamine and bromoacetyl bromide were used to produce the above compound in the same way as Reference Example 8.

Reference Example 21

Synthesis of N-(2,4,6-trimethylphenyl)-4-bromobutylamide (21)

2,4,6-trimethylaniline and 4-bromobutyryl bromide were used to produce the above compound in the same way as Reference Example 8.

Reference Example 22

Synthesis of 4-chlorobutyryl-3,4-dihydro-2H-1,4-benzoxazine (22)

3,4-dihydro-2H-1,4-benzoxazine [E. Honkanen et al.; Acta Chem. Scand., 14, 1214 (1960); U.S. 3911126] and 4-chlorobutyryl choride were used to produce the above compound in the same way as Reference Example 8.

Reference Example 23

Synthesis of N-phenyl-2-bromoacetamide (23)

Aniline and bromoacetyl bromide were used to produce the above compound in the same way as Reference Example 8.

Reference Example 24

Synthesis of N-(2,6-diisopropylphenyl)-2-bromoacetamide (24)

2,6-diisopropylaniline and bromoacetyl bromide were used to produce the above compound in the same way as Reference Example 8.

Reference Example 25

Synthesis of N-methyl-N-(1-phenylvinyl)-2-bromoacetamide (25)

N-methyl-N-(1-phenylvinyl)amine and bromoacetyl bromide were used to produce the above compound in the same way as Reference Example 8.

Reference Example 26

Synthesis of 1-cyanomethyl-4-(4-phenoxyphenyl)piperidine (26)

To an 8 ml dimethylformamide solution of 300 mg of the compound (4) synthesized in Reference Example 4 were added 93 mg of chloroacetonitrile, 355 mg of sodium iodide, and 196 mg of potassium carbonate. This was then heated at reflux for 2 hours. To the reaction was added 10 ml of ice water, then extraction was performed with ethyl acetate. The extract was dried, filtered, then concentrated under reduced pressure to obtain a residue which was then purified by silica gel column chromatography (methylene chloride:methanol =30:1) to obtain the above-identified compound (26) in an amount of 313 mg (yield of 91%).

Reference Example 27

Synthesis of 1-(2-5 aminoethyl)-4-(4-phenoxyphenyl)piperidine (27)

To a 4 ml tetrahydrofuran solution of 310 mg of the compound (26) synthesized in Reference Example 26 was gradually added under ice cooling an 8 ml tetrahydrofuran suspension of 121 mg of lithium aluminum hydride. This was stirred at room temperature for 2 hours then a 5% aqueous solution of sodium hydroxide was carefully added dropwise. The reaction was filtered by cellite and the result was washed with ether. The filtrate was concentrated to obtain a residue which was then purified by silica gel column chromatography (methylene chloride:methanol=10:1) to obtain the above-identified compound (27) in an amount of 249 mg (yield of 79%).

Example 1

Synthesis of 5-[2-(4-(4-phenoxyphenyl)piperidin-1-yl)acetylamino]-2,3,4,5-tetrahydro-1-benzoxepine (28)

To a 5 ml acetonitrile solution of 190 mg of the compound (8) synthesized in Reference Example 8 were added 184 mg of the compound (4) synthesized in Reference Example 4 and 0.14 ml of triethylamine. This was heated at reflux for 3 hours. To the reaction was added 10 ml of ice water, then extraction was performed with ethyl acetate. The extract was dried, filtered, then concentrated under reduced pressure to obtain a residue which was then purified by silica gel column chromatography (methylene chloride:methanol=25:1) to obtain the above-identified compound (28) in an amount of 300 mg (yield of 98%).

Example 2

Synthesis of 5-[4-(4-(4-phenoxyphenyl)-1,2,3,6-tetrahydropyridine-1-yl)butyrylamino]-2,3,4,5-tetrahydro-1-benzoxepine (29)

The compound (9) synthesized in Reference Example 9 and the compound (3) synthesized in Reference Example 3 were used to produce the above compound in the same way as Example 1.

Example 3

Synthesis of 5-[4-(4-(4-phenoxyphenyl)piperidin-1-yl)butyrylamino]-2,3,4,5-5 tetrahydro-1-benzoxepine (30)

The compound (9) synthesized in Reference Example 9 and the compound (4) synthesized in Reference Example 4 were used to produce the above compound in the same way as Example 1.

Example 4

Synthesis of 5-[3-(4-(4-(4-fluorophenyl)methylphenyl)piperazin-1-yl) propylsulfamoyl]-2,3,4,5-tetrahydro-1-benzoxepine (31)

The compound (10) synthesized in Reference Example 10 and the compound (5) synthesized in Reference Example 5 were used to produce the above compound in the same way as Example 1.

Example 5

Synthesis of 2-benzyl-1-[4-(4-(4-phenoxyphenyl)-1,2,3,6-tetrahydropyridin-1-yl) butyrylamino]benzene (32)

The compound (11) synthesized in Reference Example 11 and the compound (3) synthesized in Reference Example 3 were used to produce the above compound in the same way as Example 1.

Example 6

Synthesis of 2-benzyl-1-[4-(4-(4-phenoxyphenyl)piperidin-1-yl)butyrylamino]benzene (33)

The compound (11) synthesized in Reference Example 11 and the compound (4) synthesized in Reference Example 4 were used to produce the above compound in the same way as Example 1.

Example 7

Synthesis of 2-benzyl-1-[4-(4-(4-(4-fluorophenyl)methylphenyl)piperazin-1-yl)butyrylamino]benzene (34)

The compound (11) synthesized in Reference Example 11 and the compound (5) synthesized in Reference Example 5 were used to produce the above compound in the same way as Example 1.

Example 8

Synthesis of 2-benzyl-1-[4-(4-(4-(4-fluorophenyl)methylphenyl)piperidin-1-yl)butyrylamino]benzene (35)

The compound (11) synthesized in Reference Example 11 and the compound (7) synthesized in Reference Example 7 were used to produce the above compound in the same way as Example 1.

Example 9

Synthesis of 2-benzyl-1-[6-(4-(4-phenoxyphenyl)-1,2,3,6-tetrahydropyridine-1-yl)hexanoylamino]benzene (36)

The compound (12) synthesized in Reference Example 12 and the compound (3) synthesized in Reference Example 3 were used to produce the above compound in the same way as Example 1.

Example 10

Synthesis of 2-benzyl-1-[6-(4-(4-phenoxyphenyl)piperidin-1-yl)hexanoylamino]benzene (37)

The compound (12) synthesized in Reference Example 12 and the compound (4) synthesized in Reference Example 4 were used to produce the above compound in the same way as Example 1.

Example 11

Synthesis of 2-benzyl-1-[6-(4-(4-(4-fluorophenyl)methylphenyl)piperazin-1-yl)hexanoylamino]benzene (38)

The compound (12) synthesized in Reference Example 12 and the compound (5) synthesized in Reference Example 5 were used to produce the above compound in the same way as Example 1.

Example 12

Synthesis of 2-benzyl-1-[2-(4-(4-phenoxyphenyl)piperidin-1-yl)acetylamino]-6-methylbenzene (39)

The compound (13) synthesized in Reference Example 13 and the compound (4) synthesized in Reference Example 4 were used to produce the above compound in the same way as Example 1.

Example 13

Synthesis of 2-benzyl-1-[2-(4-(4-(4-fluorophenyl)methylphenyl)piperazin-1-yl)acetytamino]-6-methylbenzene (40)

The compound (13) synthesized in Reference Example 13 and the compound (5) synthesized in Reference Example 5 were used to produce the above compound in the same way as Example 1.

Example 14

Synthesis of 2-benzyl-1-[4-(4-(4-phenoxyphenyl)piperidin-1-yl)butyrylamino]-6-methylbenzene (41)

The compound (14) synthesized in Reference Example 14 and the compound (4) synthesized in Reference Example 4 were used to produce the above compound in the same way as Example 1.

Example 15

Synthesis of 2-benzyl-1-[4-(4-(4-(4-fluorophenyl)methylphenyl)piperazin-1-yl)butyrylamino]-6-methylbenzene (42)

The compound (14) synthesized in Reference Example 14 and the compound (5) synthesized in Reference Example 5 were used to produce the above compound in the same way as Example 1.

Example 16

Synthesis of N-(2,6-dimethylphenyl)-4-(4-phenoxyphenyl)-1-piperidinacetamide (43)

The compound (18) synthesized in Reference Example 18 and the compound (4) synthesized in Reference Example 4 were used to produce the above compound in the same way as Example 1.

Example 17

Synthesis of N-(2,6-dimethylphenyl)-1-[4-(4-fluorophenyl)methylphenyl]-4-piperazinacetamide (44)

The compound (18) synthesized in Reference Example 18 and the compound (5) synthesized in Reference Example 5 were used to produce the above compound in the same way as Example 1.

Example 18

Synthesis of N-(2,4,6-trimethylphenyl)-4-[4-(4-fluorophenyl)methylphenyl]-1-(1,2,3,6-tetrahydropyridin)acetamide (45)

N-(2,4,6-trimethylphenyl)-2-bromoacetamide [U.S. Pat. No. 5,028,610] and the compound (6) synthesized in Reference Example 6 were used to produce the above compound in the same way as Example 1.

Example 19

Synthesis of N-(2,4,6-trimethylphenyl)-4-[4-(4-fluorophenyl)methylphenyl]-1-piperidinacetamide (46)

N-(2,4,6-trimethylphenyl)-2-bromoacetamide [U.S. Pat. No. 5,028,610] and the compound (7) synthesized in Reference Example 7 were used to produce the above compound in the same way as Example 1.

Example 20

Synthesis of 2,6-dimethyl-1-[4-(4-(4-phenoxyphenyl)piperidin-1-yl)butyrylamino]benzene (47)

The compound (19) synthesized in Reference Example 19 and the compound (4) synthesized in Reference Example 4 were used to produce the above compound in the same way as Example 1.

Example 21

Synthesis of 2,6-dimethyl-1-[4-(4-(4-fluorophenyl)methylphenyl)piperazin-1-yl)butyrylamino]benzene (48)

The compound (19) synthesized in Reference Example 19 and the compound (5) synthesized in Reference Example 5 were used to produce the above compound in the same way as Example 1.

Example 22

Synthesis of 2,4,6-trimethyl-1-[4-(4-(4-fluorophenyl)methylphenyl)piperidine-1-yl)butyrylamino]benzene (49)

The compound (21) synthesized in Reference Example 21 and the compound (7) synthesized in Reference Example 7 were used to produce the above compound in the same way as Example 1.

Example 23

Synthesis of 5-[2-(4-(4-(4-fluorophenyl)methylphenyl)piperazin-1-yl)acetyl]-2,3,4,5-tetrahydro-1,5-benzoxazepine (50)

The compound (15) synthesized in Reference Example and the compound (5) synthesized in Reference Example were used to produce the above compound in the same way as Example 1.

Example 24

Synthesis of 5-[4-(4-(4-phenoxyphenyl)piperidin-1-yl)butyryl]-2,3,4,5-tetrahydro-1,5-benzoxazepine (51)

The compound (16) synthesized in Reference Example 16 and the compound (4) synthesized in Reference Example 4 were used to produce the above compound in the same way as Example 1.

Example 25

Synthesis of 5-[4-(4-(4-phenoxyphenyl)piperazin-1-yl)butyryl]2,3,4,5-tetrahydro-1,5-benzoxazepine (52)

The compound (16) synthesized in Reference Example 16 and 1-(4-phenoxylphenyl)piperazine [DE 2631885] were used to produce the above compound in the same way as Example 1.

Example 26

Synthesis of 5-[4-(4-(4-(4-fluorophenyl)methylphenyl)piperazin-1-yl)butyryl]-2,3,4,5-tetrahydro-1,5-benzoxazepine (53)

The compound (16) synthesized in Reference Example 16 and the compound (5) synthesized in Reference Example 5 were used to produce the above compound in the same way as Example 1.

Example 27

Synthesis of 5-[4-(4-(4-(4-fluorophenyl)methylphenyl)piperidin-1-yl)butyryl]-2,3,4,5-tetrahydro-1,5-benzoxazepine (54)

The compound (16) synthesized in Reference Example 16 and the compound (7) synthesized in Reference Example 7 were used to produce the above compound in the same way as Example 1.

Example 28

Synthesis of 5-[3-(4-(4-(4-fluorophenyl)methylphenyl)piperazin-1-yl)propyl]sulfonyl-2,3,4,5-tetrahydro-1,5-benzoxazepine (55)

The compound (17) synthesized in Reference Example 17 and the compound (5) synthesized in Reference Example 5 were used to produce the above compound in the same way as Example 1.

Example 29

Synthesis of N-(trans-2-phenyl-1-cyclopropyl)-4-(4-phenoxyphenyl)-1-piperidinacetamide (56)

The compound (20) synthesized in Reference Example 20 and the compound (4) synthesized in Reference Example 4 were used to produce the above compound in the same way as Example 1.

Example 30

Synthesis of N-(trans-2-phenyl-1-cyclopropyl)-4-[4-(4-fluorophenyl)methylphenyl]-1-piperidinacetamide (57)

The compound (20) synthesized in Reference Example 20 and the compound (7) synthesized in Reference Example 7 were used to produce the above compound in the same way as Example 1.

Example 31

Synthesis of 4-[4-(4-(4-fluorophenyl)methylphenyl)piperidin-1-yl)butyryl]-3,4-dihydro-2H-1,4-benzoxazine (58)

The compound (22) synthesized in Reference Example 22 and the compound (7) synthesized in Reference Example 7 were used to produce the above compound in the same way as Example 1.

Example 32

Synthesis of N-phenyl-4-(4-phenoxyphenyl)-1-piperidinacetamide (59)

The compound (4) synthesized in Reference Example 4 and the compound (23) synthesized in Reference Example 23 were used to produce the above compound in the same way as Example 1.

Example 33

Synthesis of N-phenyl-4-[4-(4-fluorophenyl) methylphenyl]-1-piperidinacetamide (60)

The compound (7) synthesized in Reference Example 7 and the compound (23) synthesized in Reference Example 23 were used to produce the above compound in the same way as Example 1.

Example 34

Synthesis of N-(2,6-diisopropylphenyl)-4-(4-phenoxyphenyl)-1-piperidinacetamide (61)

The compound (4) synthesized in Reference Example 4 and the compound (24) synthesized in Reference Example 24 were used to produce the above compound in the same way as Example 1.

Example 35

Synthesis of 1-(2-benzoylaminoethyl)-4-(4-phenoxyphenyl)piperidine (62)

To a 20 ml methylene chloride solution of 675 mg of the compound (27) synthesized in Reference Example 27 were added dropwise under ice cooling 0.95 ml of triethylamine and 0.27 ml of benzoyl chloride. This was stirred at room temperature for 30 minutes, then 30 ml of ice water was added and extraction was performed with methylene chloride. The extract was dried, filtered, then concentrated under reduced pressure to obtain a residue which was then purified by silica gel column chromatography (methylene chloride:methanol=30:1) to obtain the above-identified compound (62) in a yield of 630 mg (yield of 68%).

Example 36

Synthesis of 1-[2-(1-phenyl-1-cyclopropylcarboxyamino)ethyl]-4-(4-phenoxyphenyl) piperidine (63)

The compound (27) synthesized in Reference Example 27 and 1-phenyl-1-cyclopropanecarbonyl chloride were used to produce the above compound in the same way as Example 35.

Example 37

Synthesis of N-methyl-N-(1-phenylvinyl)-4-(4-phenoxyphenyl)-1-piperidinacetamide (64)

The compound (4) synthesized in Reference Example 4 and the compound (25) synthesized in Reference Example 25 were used to produce the above compound in the same way as Example 1.

The physical data of the compounds obtained in the both Reference Examples and Examples are shown in Table I.

TABLE I

| Compound no. | Chemical structure | Properties, melting point (recrystallization solvent) | IR | ¹H-NMR (CDCl₃) |
|---|---|---|---|---|
| 1 | [4-(4-phenoxyphenyl)-4-hydroxypiperidine, N-Boc] | An oily substance | (CHCl₃) 3094, 3436, 3010, 2980, 2875, 1682, 1589, 1507, 1489, 1430, 1367, 1242, 1168 | 1.48 (9H, s), 1.77–1.78 (2H, m), 1.98 (2H, t), 3.25 (2H, t), 4.24 (2H, m), 6.99 (4H, m), 7.08–7.14 (1H, m), 7.34 (2H, m), 7.40–7.46 (2H, m) |
| 2 | [4-[4-(4-fluorobenzyl)phenyl]-4-hydroxypiperidine, N-Boc] | An oily substance | (CHCl₃) 3018, 1682, 1508, 1431, 1367, 1168 | 1.48 (9H, s), 1.70–1.74 (2H, m), 1.97 (2H, t), 3.24 (2H, t), 3.94 (2H, s), 4.00 (2H, m), 6.94–6.99 (2H, m), 7.11–7.17 (4H, m), 7.38 (2H, d) |
| 3 | [4-(4-phenoxyphenyl)-1,2,3,6-tetrahydropyridine] | Colorless crystals 186–189° C. (methylene chloride/ether) | (CHCl₃) 3024, 3018, 1674, 1606, 1508, 1489, 1243 | 2.45 (2H, td), 3.11 (2H, t), 3.53 (2H, dd), 6.09 (1H, m), 6.94–7.13 (5H, m), 7.29–7.39 (4H, m) |
| 4 | [4-(4-phenoxyphenyl)piperidine] | Colorless crystals (hydrochloride) 84–87° C. (methylene chloride/ether) | (KBr) (hydrochloride) 3024, 2960, 2712, 1590, 1508, 1489, 1241, 1208 | 1.61 (2H, ddd), 1.83 (2H, d), 2.60 (1H, tt), 2.74 (2H, td), 3.18 (2H, d), 6.94 (2H, d), 7.00 (2H, d), 7.07 (1H, t), 7.17 (2H, d), 7.31 (2H, t) |
| 5 | [4-(4-fluorobenzyl)phenylpiperazine] | Colorless crystals (dihydrochloride) 139–141° C. (methanol/ether) | (KBr) (dihydrochloride) 3426, 3410, 3000, 2636, 2480, 1602, 1508, 1221, 1158 | 3.03 (4H, dd), 3.11 (4H, dd), 3.87 (2H, s), 6.83–7.14 (8H, m) |

TABLE I-continued

| Compound no. | Chemical structure | Properties, melting point (recrystallization solvent) | IR (CHCl₃) | ¹H-NMR (CDCl₃) |
|---|---|---|---|---|
| 6 | [structure: 4-fluorobenzyl attached to tetrahydropyridine with NH] | Light yellow crystals | (CHCl₃) 3020, 2926, 2993, 1604, 1508, 1434, 1157, 1016, 930 | 2.43 (2H, td), 3.09 (2H, t), 3.51 (2H, dd), 3.92 (2H, s), 6.10 (1H, m), 6.94–6.98 (2H, m), 7.10–7.15 (4H, m), 7.31 (2H, d) |
| 7 | [structure: 4-fluorobenzyl attached to piperidine with NH] | An oily substance | (CHCl₃) 2930, 2337, 1603, 1508, 1446, 1318, 1016, 862, 820 | 1.57–1.66 (2H, m), 1.83 (2H, d), 2.58 (1H, tt), 2.73 (2H, d), 3.17 (2H, d), 3.91 (2H, s), 6.94–6.97 (2H, m), 7.08–7.18 (6H, m) |
| 8 | [structure: bromoacetamide on benzoxepine] | Colorless crystals | (CHCl₃) 3412, 2400, 1660, 1520, 1488, 1428, 1048, 929, 848 | 1.80 (2H, m), 2.23 (2H, m), 3.73 (1H, td), 3.88 (2H, s), 4.41 (1H, dt), 5.24 (1H, td), 7.05 (2H, dd), 7.21 (1H, d), 7.23 (1H, d) |
| 9 | [structure: 4-chlorobutyramide on benzoxepine] | Colorless crystals | 3436, 2940, 1664, 1504, 1488, 1456, 1178, 996 | 1.79 (2H, m), 2.07–2.31 (4H, m), 2.35 (2H, t), 3.45 (2H, t), 3.71 (1H, td), 4.40 (1H, dt), 5.25 (1H, td), 6.25 (1H, d), 7.04 (2H, dd), 7.19–7.25 (2H, m) |

TABLE I-continued

| | Structure | | Appearance | IR | NMR |
|---|---|---|---|---|---|
| 10 | H-N(SO₂)-(CH₂)₃-Cl attached to 4-position of 2,3,4,5-tetrahydro-1-benzoxepine | | Colorless crystals 119–120° C. (methylene chloride/ether) | 3376, 3027, 2948, 2878, 2364, 1603, 1582, 1489, 1452, 1416, 1338, 1210, 1150, 1000 | 1.78–1.89 (3H, m), 2.02–2.16 (1H, m), 2.23–2.41 (2H, m), 2.67 (1H, tt), 2.91 (1H, tt), 3.39 (2H, dt), 3.65 (1H, td), 4.43 (1H, dt), 4.64 (1H, ddd), 5.28 (1H, d), 7.03–7.10 (2H, m), 7.24–7.28 (2H, m) |
| 11 | 2-benzyl-N-(5-bromopentanoyl)aniline | | Colorless crystals | 3412, 2400, 1682, 1587, 1514, 1495, 1452, 929 | 2.13 (2H, ddd), 2.33 (2H, t), 3.44 (2H, t), 4.00 (2H, s), 6.89 (1H, brs), 7.16 (4H, d), 7.24–7.35 (5H, m), 7.83 (1H, brs) |
| 12 | 2-benzyl-N-(7-bromoheptanoyl)aniline | | Colorless crystals | 3413, 2940, 1686, 1587, 1514, 1494, 1475, 1452, 1298, 1250 | 1.43 (2H, m), 1.56 (2H, m), 1.83 (2H, m), 2.15 (2H, t), 3.38 (2H, t), 4.00 (2H, s), 6.80 (1H, brs), 7.15 (4H, d), 7.22–7.35 (4H, m), 7.87 (1H, brs) |
| 13 | N-(2-benzyl-6-methylphenyl)-2-bromoacetamide | | Colorless crystals | 3384, 2400, 1678, 1601, 1504, 1470, 1090, 1030, 929, 847 | 2.23 (3H, s), 3.93 (2H, s), 3.96 (2H, s), 7.09–7.30 (8H, m), 7.54 (1H, m) |

TABLE I-continued

| | Structure | IR | NMR | Appearance |
|---|---|---|---|---|
| 14 | [structure: 2-methyl-6-benzyl-phenyl amide of 5-chloropentanoic acid] | 3412, 2365, 1682, 1592, 1494, 1074, 1030, 812 | 2.14 (2H, m), 2.21 (3H, s), 2.45 (2H, t), 3.63 (2H, t), 3.94 (2H, s), 6.48 (1H, brs), 7.09–7.30 (8H, m) | Colorless crystals |
| 15 | [structure: N-(2-methylphenyl)-N-(3-(2-methylphenoxy)propyl) bromoacetamide type] | 3010, 2954, 1662, 1496, 1413, 1426, 1400, 1312, 1255, 1214, 1051 | 1.80–1.83 (2H, m), 2.25–2.34 (1H, m), 2.85 (1H, bt), 3.71 and 3.72 (2H, each s), 4.49 (1H, bd), 4.81 (1H, bd), 7.10–7.16 (2H, m), 7.29–7.32 (2H, m) | Colorless crystals |
| 16 | [structure] | 3026, 2982, 2670, 1608, 1565, 1503, 1470, 1264, 1218, 1212, 1044, 984, 915 | 1.75–1.84 (1H, m), 1.99–2.54 (5H, m), 2.71–2.82 (1H, m), 3.49–3.62 (2H, m), 3.66–3.75 (1H, m), 4.45 (1H, m), 4.83 (1H, m), 7.10–7.21 (3H, m), 7.24–7.31 (1H, m) | Colorless crystals |
| 17 | [structure: sulfonamide] | 3026, 2950, 2364, 2340, 1791, 1490, 1459, 1340, 1256, 1216, 1210, 1152, 1189, 1055 | 2.04–2.10 (2H, m), 2.22–2.29 (2H, m), 3.20 (2H, t), 3.62 (2H, t), 3.81 (2H, m), 4.09 (2H, m), 7.10–7.17 (2H, m), 7.26–7.28 (1H, m), 7.48–7.51 (1H, m) | Colorless crystals |
| 18 | [structure: 2,6-dimethylphenyl bromoacetamide] | 3390, 2400, 1678, 1505, 1441, 929 | 2.25 (6H, s), 4.08 (2H, s), 7.08–7.14 (3H, m), 7.71 (1H, brs) | Colorless crystals |

TABLE I-continued

| | Structure | Appearance | IR | NMR |
|---|---|---|---|---|
| 19 | (2,6-dimethylphenyl)-NH-CO-(CH2)3-Br | Colorless crystals | 3423, 1677, 1486, 1438, 1093, 1036, 931 | 2.23 (6H, s), 2.28–2.34 (2H, m), 2.62 (2H, t), 3.57 (2H, t), 6.73 (1H, brs), 7.07–7.14 (3H, m) |
| 20 | PhCH2-cyclopropyl-NH-CO-CH2-Br | An oily substance | 3413, 2399, 1674, 1605, 1520, 1428, 1031, 928, 849 | 1.22 (1H, ddd), 1.31 (1H, ddd), 2.12 (1H, m), 2.93 (1H, m), 3.88 (2H, s), 6.65 (1H, brs), 7.15–7.21 (4H, m), 7.28 (1H, t) |
| 21 | (2,4-dimethylphenyl)-NH-CO-(CH2)3-Br | Colorless crystals | 3421, 2400, 1676, 1491, 1438, 1035, 928, 852 | 2.21 (6H, s), 2.29 (3H, s), 2.3 (2H, m), 2.64 (2H, t), 3.59 (2H, t), 6.71 (1H, brs), 6.93 (2H, s) |
| 22 | benzomorpholine-N-CO-(CH2)3-Cl | An oily substance | 3019, 1654, 1497, 1397, 1257, 1225, 1207, 1058, | 2.18 (2H, tt), 2.78 (2H, t), 3.64 (2H, t), 3.95 (2H, t), 4.30 (2H, t), 6.89–6.93 (2H, m), 7.09 (1H, t), 7.28 (1H, m) |
| 23 | Ph-NH-CO-CH2-Br | Colorless crystals | 3394, 2401, 1676, 1601, 1534, 1445, 929, 850 | 4.05 (2H, s), 7.20 (1H, t), 7.39 (2H, t), 7.56 (2H, d), 8.12 (1H, brs) |
| 24 | (2,6-diisopropylphenyl)-NH-CO-CH2-Br | Colorless crystals | 3392, 3019, 2967, 2401, 1676, 1502, 1474, 1364, 1058, 932 | 1.14 (12H, d), 2.97 (2H, q), 4.02 (2H, s), 7.12 (2H, d), 7.25 (1H, t), 7.60 (1H, brs) |
| 25 | Ph-C(=N-Me)-O-CO-CH2-Br | An oily substance | 2400, 1658, 1632, 1429, 1383, 1079, 1028, 911, 849 | 3.16 (3H, s), 3.93 (2H, s), 5.42 (1H, s), 5.78 (1H, s), 7.35–7.68 (5H, m) |

TABLE I-continued

| Compound no. | Chemical structure | Properties, melting point (recrystallization solvent) | IR (KBr) | $^1$H-NMR (CDCl$_3$) | Elemental analysis (hydrochloride) |
|---|---|---|---|---|---|
| 26 | [4-(4-phenoxyphenyl)piperidine with NC-CH$_2$-N substituent] | Colorless crystals | 2407, 1654, 1560, 1508, 1490, 1420, 1208, 929 | 1.78 (2H, m), 1.91 (2H, m), 2.42–2.65 (3H, m), 2.92 (2H, m), 3.57 (2H, s), 6.95 (2H, d), 6.99 (2H, d), 7.08 (1H, t), 7.17 (2H, d), 7.32 (2H, t) | |
| 27 | [4-(4-phenoxyphenyl)piperidine with H$_2$N-CH$_2$CH$_2$-N substituent] | An oily substance | 2941, 2806, 2400, 1590, 1507, 1490, 1209, 1169, 1049, 929 | 1.70–1.90 (4H, m), 2.09 (2H, m), 2.45 (2H, t), 2.48 (1H, tt), 2.82 (2H, t), 3.01 (2H, m), 6.94 (2H, d), 7.00 (2H, d), 7.07 (1H, t), 7.18 (2H, d), 7.32 (2H, t) | |
| 28 | [4-(4-phenoxyphenyl)piperidine linked via CH$_2$-C(=O)-NH to benzoxepine] | Colorless crystals (hydrochloride) 200–202° C. (methanol/ether) | (hydrochloride) 3022, 2948, 1684, 1590, 1555, 1508, 1489, 1452, 1239 | 1.67–1.88 (6H, m), 2.15–2.33 (4H, m), 2.48 (1H, tt), 2.76 (2H, m), 2.98–3.07 (3H, m), 3.76 (1H, t), 4.36 (1H, m), 5.27 (1H, m), 6.95–7.05 (6H, m), 7.18 (4H, dd), 7.33 (2H, t), 8.07 (1H, d) | C$_{29}$H$_{32}$ClN$_2$O$_3$·1/2H$_2$O<br>    C    H    N<br>Calcd: 69.38 6.83 5.58<br>Found: 69.24 6.70 5.58 |
| 29 | [4-(4-phenoxyphenyl)-tetrahydropyridine linked via (CH$_2$)$_3$-C(=O)-NH to benzoxepine] | Colorless crystals (hydrochloride) 100–105° C. (methanol/ether) | (hydrochloride) 2940, 1658, 1505, 1488, 1245, 1056, 972 | 1.66–1.82 (2H, m), 1.90 (2H, tt), 2.14–2.25 (2H, m), 2.29 (2H, t), 2.47 (2H, t), 2.50 (2H, m), 2.65 (1H, m), 3.01–3.19 (2H, m), 3.65–3.76 (2H, m), 4.33 (1H, dt), 5.24 (1H, td), 5.97 (1H, m), 6.55 (1H, d), 6.93–7.38 (13H, m) | — |

TABLE I-continued

| | Structure | Crystals / Salt / mp / Solvent | IR | NMR | Formula / Analysis |
|---|---|---|---|---|---|
| 30 | (4-phenoxyphenyl-piperidine attached via butanamide to benzoxepine with o-tolyl) | Colorless crystals (hydrochloride) 205–210° C. (methanol/ether) | (hydrochloride) 2945, 1654, 1634, 1542, 1508, 1490, 1238, 1052, 966, 872, 776, 750, 692 | 1.67–2.03 (10H, m), 2.14–2.24 (2H, m), 2.26 (2H, t), 2.35 (2H, t), 2.45 (1H, m), 2.80 (1H, d), 3.03 (1H, d), 3.71 (1H, t), 4.37 (1H, d), 5.25 (1H, td), 6.54 (1H, d), 6.91–7.36 (13H, m) | $C_{21}H_{27}ClN_2O_2 \cdot 2/3H_2O$<br>C  H  N<br>Calcd: 69.84  7.25  5.25<br>Found: 69.76  6.78  5.30 |
| 31 | (4-fluorobenzyl-piperazine attached via propylsulfonamide to benzoxepine with o-tolyl) | Colorless crystals (dihydrochloride) 180–182° C. (methanol/ether) | (dihydrochloride) 3460, 2954, 2554, 1602, 1560, 1508, 1488, 1451, 1376, 1318, 1224, 1148, 1108, 998 | 1.61–1.63 (1H, m), 1.73–1.86 (3H, m), 2.14–2.27 (3H, m), 2.41–2.42 (5H, m), 2.60 (1H, t), 2.90 (1H, tt), 3.08 (4H, t), 3.65 (1H, td), 3.87 (2H, s), 4.42 (2H, dd), 4.65 (1H, bt), 5.54 (1H, d), 6.83 (2H, d), 6.95 (1H, t), 7.02–7.13 (5H, m), 7.21–7.24 (4H, m) | $C_{30}H_{38}Cl_2FN_2O_3S \cdot H_2O$<br>C  H  N<br>Calcd: 57.32  6.09  6.68<br>Found: 57.48  6.04  6.75 |
| 32 | (4-(4-phenoxyphenyl)-tetrahydropyridine attached via butanamide to 2-benzylaniline) | Colorless crystals (hydrochloride) 90–92° C. (methanol/ether) | (hydrochloride) 2574, 1672, 1586, 1522, 1510, 1494, 1449, 1238, 1173, 756, 695 | 1.86 (2H, m), 2.31 (2H, t), 2.47–2.52 (4H, m), 2.65 (2H, t), 3.12 (2H, dd), 3.97 (2H, s), 5.99 (1H, m), 6.92–7.33 (17H), 7.72 (1H, d), 7.90 (1H, m) | $C_{34}H_{36}ClN_2O_2 \cdot 4/5H_2O$<br>C  H  N<br>Calcd: 73.78  6.66  5.06<br>Found: 73.54  6.43  5.08 |
| 33 | (4-(4-phenoxyphenyl)-piperidine attached via butanamide to 2-benzylaniline) | Colorless crystals (hydrochloride) 186–188° C. (methanol/ether) | (hydrochloride) 3229, 2652, 1661, 1587, 1531, 1508, 1490, 1453, 1229, 749, 693 | 1.61 (2H, m), 1.75–1.85 (4H, m), 2.00 (2H, td), 2.32 (2H, t), 2.38–2.50 (3H, m), 2.94 (2H, d), 4.01 (2H, s), 6.91 (2H, d), 6.96–7.37 (15H, m), 8.27 (1H, m) | $C_{34}H_{37}ClN_2O_2 \cdot H_2O$<br>C  H  N<br>Calcd: 73.04  7.03  5.01<br>Found: 73.09  7.04  5.04 |

TABLE I-continued

| | | | | |
|---|---|---|---|---|
| 34 | 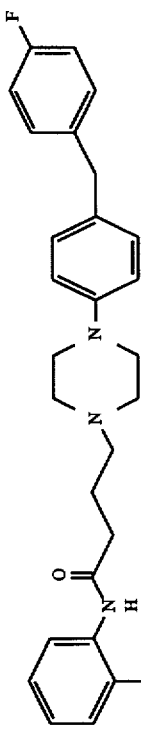 | Colorless crystals (dihydrochloride) 108–110° C. (methanol/ether) | (dihydrochloride) 2588, 1658, 1601, 1585, 1520, 1504, 1452, 1296, 1218, 1184, 1157, 807, 756, 700 | 1.80 (2H, m), 2.27 (2H, t), 2.39 (2H, t), 2.52 (4H, t), 3.08 (4H, t), 3.87 (2H, s), 3.99 (2H, s), 6.80–7.32 (16H, m), 7.51 (1H, m), 7.73 (1H, d) | — |
| 35 | 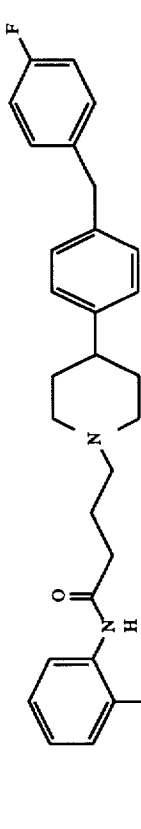 | Colorless crystals (hydrochloride) 168–170° C. (methanol/ether) | (hydrochloride) 3442, 2920, 2668, 2362, 2332, 1666, 1652, 1587, 1526, 1506, 1451, 1220, 1156, 1072 | 1.26 (1H, m), 1.64 (1H, m), 1.74–1.89 (5H, m), 2.02 (1H, bt), 2.31 (1H, bt), 2.40–2.46 (4H, m), 2.93–2.95 (2H, m), 3.91 (2H, s), 4.01 (2H, s), 6.94–7.29 (16H, m), 7.69 (1H, bd), 8.16 (1H, bs) | $C_{36}H_{39}ClFN_2O \cdot H_2O$ C H N Calcd: 73.09 6.66 4.87 Found: 73.30 6.80 4.87 |
| 36 |  | Colorless crystals (hydrochloride) 140–142° C. (methanol/ether) | (hydrochloride) 2551, 1660, 1589, 1522, 1450, 1235, 1172, 1106, 1073, 872, 812, 758, 692 | 1.34 (2H, m), 2.16 (2H, m), 2.44 (2H, t), 2.56 (2H, m), 2.69 (2H, m), 3.14 (2H, m), 3.99 (2H, s), 6.01 (1H, m), 6.87–7.36 (18H, m), 7.87 (1H, d) | $C_{36}H_{39}ClN_2O_2 \cdot 1/5H_2O$ C H N Calcd: 75.76 6.96 4.91 Found: 75.86 6.88 4.94 |
| 37 | 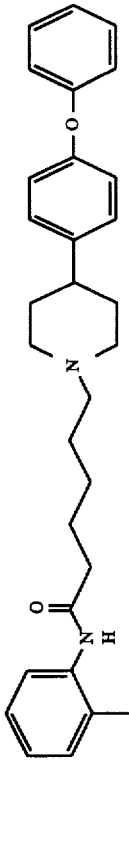 | Colorless crystals (hydrochloride) 185–187° C. (methanol/ether) | (hydrochloride) 2948, 1682, 1588, 1509, 1489, 1451, 1240, 748, 696 | 1.32 (2H, m), 1.57 (4H, td), 1.85 (4H, dd), 2.03–2.13 (2H, m), 2.17 (2H, t), 2.39 (2H, t), 2.50 (1H, m), 3.09 (2H, d), 4.00 (2H, s), 6.91–7.38 (18H, m), 7.86 (1H, d) | $C_{39}H_{44}ClN_2O_2 \cdot 1/3H_2O$ C H N Calcd: 75.18 7.30 4.87 Found: 75.17 7.19 4.87 |

TABLE I-continued

| # | Structure | Crystal/mp | IR | NMR | Analysis |
|---|---|---|---|---|---|
| 38 | 4-F-benzyl-piperazinyl-pentanoyl-(2-benzylphenyl)amide | Colorless crystals (hydrochloride) 150–153° C. (methanol/ether) | (hydrochloride) 2394, 2328, 1664, 1602, 1586, 1510, 1448, 1218, 1157, 813, 739, 702 | 1.25–1.39 (2H, m), 1.53 (4H, m), 2.15 (2H, t), 2.35 (2H, t), 2.57 (4H, t), 3.16 (4H, t), 8.86 (2H, s), 3.98 (2H, s), 6.83–7.34 (17H, m), 7.86 (1H, d) | — |
| 39 | 4-phenoxyphenyl-piperidinyl-acetyl-(2-benzyl-6-methylphenyl)amide | Colorless crystals (hydrochloride) 112–115° C. (methanol/ether) | (hydrochloride) 3176, 3023, 1686, 1590, 1537, 1508, 1490, 1453, 1239, 748, 696 | 1.51 (2H, ddd), 1.78 (2H, d), 2.25 (3H, s), 2.32 (2H, td), 2.44 (1H, tt), 2.92 (2H, d), 3.10 (2H, s), 3.99 (2H, s), 6.92–7.37 (17H, m), 8.63 (1H, brs) | $C_{33}H_{35}ClN_2O_2 \cdot 6/5H_2O$<br>　　　C　　H　　N<br>Calcd: 72.23　6.87　5.11<br>Found: 72.28　6.61　5.12 |
| 40 | 4-(4-F-benzyl)piperazinyl-acetyl-(2-benzyl-6-methylphenyl)amide | Colorless crystals (dihydrochloride) 125–127° C. (methanol/ether) | (dihydrochloride) 3166, 3009, 2434, 1684, 1601, 1516, 1454, 1222, 1157, 814, 772, 704 | 2.24 (3H, s), 2.64 (4H, t), 3.00 (4H, t), 3.12 (2H, s), 3.87 (2H, s), 3.98 (2H, s), 6.81 (2H, dd), 6.96 (2H, m), 7.03–7.34 (12H, m), 8.48 (1H, brs) | $C_{33}H_{36}Cl_2FN_2O \cdot 7/4H_2O$<br>　　　C　　H　　N<br>Calcd: 69.36　6.31　7.35<br>Found: 69.30　6.28　7.32 |
| 41 | 4-phenoxyphenyl-piperidinyl-butanoyl-(2-benzyl-6-methylphenyl)amide | Colorless crystals (hydrochloride) 95–97° C. (methanol/ether) | (hydrochloride) 3180, 2953, 2524, 1676, 1590, 1493, 1238, 1170, 869, 750, 710, 694 | 1.59 (2H, m), 1.77 (2H, d), 1.91 (2H, tt), 2.09 (2H, t), 2.25 (3H, s), 2.44 (1H, m), 2.46 (2H, t), 2.51 (2H, t), 3.01 (2H, d), 3.97 (2H, s), 6.89 (2H, d), 6.93 (2H, d), 6.98 (2H, d), 7.04–7.19 (7H, m), 7.26 (2H, t), 7.32 (2H, t), 8.43 (1H, brs) | — |

TABLE I-continued

| | Structure | | | |
|---|---|---|---|---|
| 42 | (4-fluorobenzyl-piperazine-butanamide with 2-benzyl phenyl) | Colorless crystals (dihydrochloride) 118–120° C. (methanol/ether) | (dihydrochloride) 3284, 3000, 2369, 1646, 1524, 1224, 1170, 872, 778, 702 | 1.74 (2H, m), 2.07 (3H, s), 2.25 (2H, t), 2.32 (2H, t), 2.39 (4H, t), 2.91 (4H, t), 3.72 (2H, s), 3.80 (2H, s), 6.66 (2H, d), 6.80 (1H, t), 6.89–7.13 (13H, m), 7.28 (1H, brs) | $C_{28}H_{40}Cl_2FN_3O$<br>C  H  N<br>Calcd: 69.07 6.62 6.90<br>Found: 69.11 6.64 6.88 |
| 43 | (4-phenoxyphenyl-piperidinyl-acetamide with 2,6-dimethylphenyl) | Colorless crystals (hydrochloride) 118–120° C. (methanol/ether) | (hydrochloride) 3182, 2944, 1684, 1590, 1536, 1507, 1490, 1242, 1157, 814, 776, 747, 694 | 1.87 (2H, ddd), 2.00 (2H, d), 2.25 (6H, s), 2.45 (2H, td), 2.56 (1H, t), 3.15 (2H, d), 3.23 (2H, s), 6.96 (2H, d), 7.01 (2H, d), 7.07–7.10 (4H, m), 7.19 (2H, d), 7.32 (2H, t), 8.76 (1H, brs) | $C_{27}H_{31}ClN_2O_2 \cdot 5/4H_2O$<br>C  H  N<br>Calcd: 68.49 6.13 5.92<br>Found: 68.29 6.77 5.90 |
| 44 | (4-fluorobenzyl-phenyl-piperazinyl-acetamide with 2,6-dimethylphenyl) | Colorless crystals (dihydrochloride) 135–138° C. | (dihydrochloride) 3158, 3004, 2369, 1689, 1601, 1536, 1513, 1472, 1350, 1289, 1222, 1157, 778 | 2.24 (6H, s), 2.86 (4H, t), 3.24 (4H, t), 3.27 (2H,s), 3.88 (2H, s), 6.87 (2H, d), 6.95 (2H, t), 7.06–7.14 (7H, m), 8.64 (1H, brs) | $C_{27}H_{29}Cl_2N_2FO$<br>C  H  N<br>Calcd: 64.28 6.39 8.33<br>Found: 64.11 6.40 8.28 |
| 45 | (4-fluorobenzyl-phenyl-tetrahydropyridinyl-acetamide with 2,4,6-trimethylphenyl) | Colorless crystals (hydrochloride) 130–132° C. (methanol/ether) | (hydrochloride) 3166, 2917, 2534, 1676, 1602, 1560, 1506, 1438, 1222, 1157, 847, 808 | 2.20 (6H, s), 2.26 (3H, s), 2.62 (2H, m), 2.94 (2H, t), 3.32 (2H, s), 3.36 (2H, s), 3.94 (2H, s), 6.08 (1H, m), 6.90 (2H, d), 6.96 (2H, m), 7.11–7.15 (4H, m), 7.33 (2H, d), 8.64 (1H, brs) | $C_{29}H_{32}ClFN_2O \cdot 0.1/2H_2O$<br>C  H  N<br>Calcd: 71.37 6.82 5.74<br>Found: 71.32 6.82 5.69 |
| 46 | (4-fluorobenzyl-phenyl-piperidinyl-acetamide with 2,4,6-trimethylphenyl) | Colorless crystals (hydrochloride) 118–120° C. (methanol/ether) | (hydrochloride) 3182, 2926, 1684, 1602, 1541, 1508, 1440, 1221, 1157, 854, 820 | 1.78 (2H, ddd), 1.91 (2H, m), 2.20 (6H, s), 2.27 (3H, s), 2.43 (2H, td), 2.54 (1H, t), 3.13 (2H, m), 3.21 (2H, s), 3.92 (2H, s), 6.91 (2H, s), 6.96 (2H, m), 7.10–7.16 (6H, m), 8.68 (1H, brs) | $C_{29}H_{34}ClFN_2O \cdot H_2O$<br>C  H  N<br>Calcd: 69.79 7.27 5.61<br>Found: 69.97 7.25 5.62 |

TABLE I-continued

| No. | Structure | Appearance (salt form) mp (solvent) | IR | ¹H NMR | Formula / Analysis |
|---|---|---|---|---|---|
| 47 | (2,6-dimethylphenyl amide, butyl chain, piperidine, 4-phenoxyphenyl) | Colorless crystals (hydrochloride) 206–208° C. (methanol/ether) | (hydrochloride) 3208, 2933, 2486, 1678, 1590, 1522, 1486, 1238, 774, 744, 691 | 1.64 (2H, m), 1.82 (2H, d), 2.01 (2H, m), 2.20 (2H, d), 2.26 (3H, s), 2.28 (3H, s), 2.48 (1H, t), 2.60 (2H, t), 2.65 (2H, t), 3.16 (2H, d), 6.88 (2H, dd), 6.97 (2H, d), 7.06–7.08 (4H, m), 7.31 (2H, t), 9.20 (1H, brs) | C₂₉H₃₅ClN₂O₂·1/3H₂O  C  H  N<br>Calcd: 71.82 7.41 5.78<br>Found: 71.66 7.27 5.83 |
| 48 | (2,6-dimethylphenyl amide, butyl chain, piperazine, 4-fluorobenzyl) | Colorless crystals (dihydrochloride) 189–191° C. | (dihydrochloride) 3246, 2932, 2484, 1676, 1648, 1512, 1458, 1224, 1157, 814, 767 | 2.00 (2H, m), 2.23 (6H, s), 2.52 (2H, t), 2.56 (2H, t), 2.64 (4H, t), 3.13 (4H, t), 3.86 (2H, s), 6.82 (2H, d), 6.94 (1H, t), 7.02–7.12 (6H, m), 7.25 (1H, brs) | — |
| 49 | (2,6-dimethylphenyl amide, butyl chain, piperidine, 4-fluorobenzyl-phenyl) | Colorless crystals (hydrochloride) 219–220° C. (methanol/ether) | (hydrochloride) 3218, 2920, 2484, 1676, 1603, 1508, 1439, 1221, 1156, 856 | 1.8 (2H, m), 1.95 (2H, m), 2.23 (6H, s), 2.29 (3H, s), 2.15–2.45 (4H, m), 2.6 (4H, m), 3.12 (2H, m), 3.91 (2H, s), 6.85–7.2 (11H, m) | C₃₁H₃₉ClFN₂O  C  H  N<br>Calcd: 73.14 7.52 5.50<br>Found: 73.09 7.49 5.50 |
| 50 | (benzoxepine, piperazine, 4-fluorobenzyl, acetamide) | Colorless crystals (dihydrochloride) 149–151° C. (methanol/ether) | (dihydrochloride) 3001, 2958, 2361, 1684, 1670, 1506, 1460, 1376, 1254, 1219 | 1.81 (1H, m), 2.29 (1H, m), 2.54 (4H, bt), 2.78 (1H, bt), 2.90–2.94 (1H, m), 3.09–3.10 (4H, m), 3.47 (1H, m), 3.71 (1H, bt), 3.85 (2H, s), 4.46 (1H, bd), 4.85 (1H, bd), 6.80 (2H, d), 6.93 (1H, td), 6.99–7.12 (5H, m), 7.22–7.25 (4H, m) | C₂₄H₃₂Cl₂FN₂O₂  C  H  N<br>Calcd: 63.16 6.06 7.89<br>Found: 63.25 6.02 8.01 |
| 51 | (benzoxepine, butyl chain, piperidine, 4-phenoxyphenyl) | Colorless crystals (hydrochloride) 217–220° C. (methanol/ether) | (hydrochloride) 2948, 2479, 1651, 1588, 1492, 1408, 1302, 1241, 1171, 1058, 871, 771, 694 | 1.63–1.88 (4H, m), 1.98–2.15 (4H, m), 2.18–2.38 (4H, m), 2.39–2.52 (1H, m), 2.76 (1H, m), 2.91–3.07 (4H, m), 3.71 (1H, m), 4.45 (1H, m), 4.86 (1H, m), 6.92–7.35 (13H, m) | C₂₉H₃₉ClN₂O₂·1/3H₂O  C  H  N<br>Calcd: 70.24 7.01 5.49<br>Found: 70.05 6.93 5.40 |

TABLE I-continued

| # | Structure | Crystal form | IR | NMR | Elemental Analysis |
|---|---|---|---|---|---|
| 52 | (4-phenoxyphenyl-piperazine with chromane amide) | Colorless crystals (dihydrochloride) 185–188° C. (methanol/ether) | (dihydrochloride) 2952, 2428, 1654, 1589, 1508, 1490, 1454, 1406, 1240, 973, 761 | 1.77 (2H, m), 2.28–2.32 (4H, m), 2.51 (4H, m), 2.76 (1H, m), 3.08 (4H, t), 3.71 (1H, m), 4.45 (1H, m), 4.87 (1H, m), 6.87–7.30 (13H, m) | — |
| 53 | (4-fluorobenzyl-phenyl-piperazine with chromane amide) | Colorless crystals (dihydrochloride) 192–193° C. (methanol/ether) | dihydrochloride 3446, 3418, 2904, 2356, 2332, 1734, 1658, 1643, 1560, 1496, 1456, 1404, 1220, 1089, 1042 | 1.33 (1H, m), 1.73–1.83 (2H, m), 2.12 (1H, m), 2.20–2.32 (4H, m), 2.45–2.53 (4H, m), 2.75 (1H, m), 3.08 (4H, t), 3.70 (1H, m), 3.86 (2H, s), 4.45 (1H, m), 4.84 (1H, m), 6.83 (2H, d), 6.94 (2H, t), 7.02–7.25 (9H, m) | $C_{20}H_{36}Cl_2FN_2O_2 \cdot 1/4H_2O$<br>　　　C　　H　　N<br>Calcd: 63.77　6.51　7.44<br>Found: 63.88　6.37　7.34 |
| 54 | (4-fluorobenzyl-phenyl-piperidine with chromane amide) | Colorless crystals (hydrochloride) 164–165° C. (methylene chloride/ether/hexane) | hydrochloride 3434, 2930, 2582, 2298, 1753, 1654, 1540, 1508, 1496, 1411, 1253, 1056, 972 | 1.73–1.81 (7H, m), 1.98 (1H, m), 2.09 (1H, m), 2.23–2.30 (4H, m), 2.42 (1H, m), 2.76 (1H, bd), 2.89 (1H, m), 2.96 (1H, m), 3.49 (1H, s), 3.71 (1H, bt), 3.91 (2H, s), 4.43 (1H, bd), 4.84 (1H, bd), 6.96 (2H, t), 7.07–7.23 (10H, m) | $C_{21}H_{34}ClFN_2O_2 \cdot 1/2H_2O$<br>　　　C　　H　　N<br>Calcd: 69.98　6.82　5.26<br>Found: 70.11　6.87　5.20 |
| 55 | (4-fluorobenzyl-phenyl-piperazine with chromane sulfonamide) | Colorless crystals (hydrochloride) 207–209° C. (methanol/ether) | hydrochloride 3425, 2921, 2840, 2544, 2363, 2356, 2345, 1614, 1506, 1492, 1456, 1338, 1256, 1151, 1089, 1058 | 1.94–2.01 (2H, m), 2.05–2.08 (2H, m), 2.43 (2H, t), 2.53 (4H, m), 3.09–3.15 (6H, m), 3.79 (2H, m), 3.86 (2H, s), 4.08 (2H, m), 6.83 (3H, d), 6.94 (1H, t), 7.03–7.13 (6H, m), 7.24 (1H, dd), 7.51 (1H, dd) | $C_{29}H_{36}N_2O_2ClFS \cdot 1/2H_2O$<br>　　　C　　H　　N<br>Calcd: 61.20　6.38　7.38<br>Found: 61.42　6.30　7.27 |

TABLE I-continued

| | | | | |
|---|---|---|---|---|
| 56 | 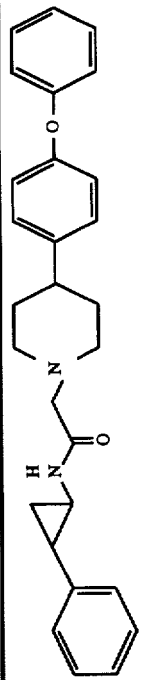 | Colorless crystals (fumarate) 170–172° C. (methanol/ether) | (fumarate) 3038, 1692, 1587, 1557, 1508, 1490, 1245, 974, 748, 694 | 1.21 (1H, ddd), 1.30 (1H, ddd), 1.74 (2H, ddd), 1.88 (2H, dd), 2.07 (1H, m), 2.30 (2H, td), 2.51 (1H, t), 2.93–2.98 (3H, m), 3.03 (2H, s), 6.95–7.01 (4H, m), 7.09 (1H, t), 7.11–7.20 (6H, m), 7.28–7.35 (3H, t), 7.39 (1H, brs) | C₃₂H₃₄N₂O₂ (fumarate)<br>    C   H   N<br>Calcd: 70.83 6.32 5.16<br>Found: 70.67 6.32 5.15 |
| 57 | 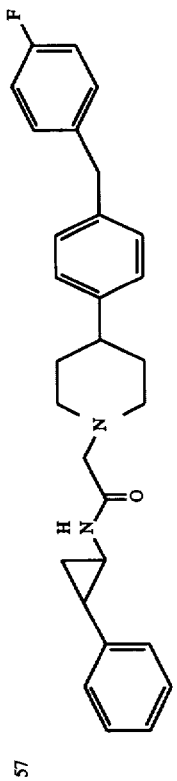 | Colorless crystals (fumarate) 168–170° C. (methanol/ether) | (fumarate) 3043, 1686, 1575, 1554, 1504, 1404, 1257, 1219, 1157, 974, 746, 698 | 1.21 (1H, dd), 1.29 (1H, ddd), 1.73 (2H, ddd), 1.85 (2H, dd), 2.08 (1H, m), 2.28 (2H, td), 2.49 (1H, t), 2.91–2.98 (3H, m), 3.02 (2H, s), 3.93 (2H, s), 6.97 (2H, t), 7.10–7.20 (10H, m), 7.28 (1H, t), 7.38 (1H, brs) | C₃₃H₃₅N₂FO₅ (fumarate).1/4H₂O<br>    C   H   N<br>Calcd: 70.38 6.35 4.97<br>Found: 70.62 6.34 4.95 |
| 58 | 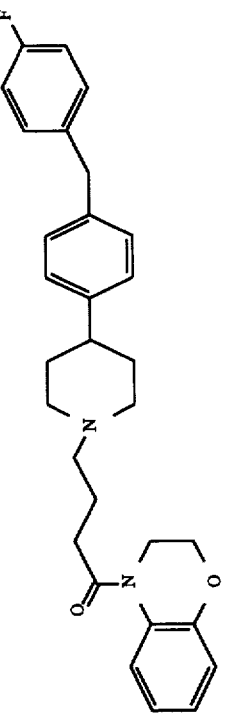 | Colorless crystals (hydrochloride) 155–157° C. (methanol/ether) | (hydrochloride) 3421, 2930, 2544, 1660, 1601, 1508, 1495, 1402, 1252, 1220, 1058, 756 | 1.75–1.88 (4H, m), 1.93–1.96 (2H, m), 2.06 (2H, m), 2.44–2.46 (3H, m), 2.66 (2H, t), 3.01 (2H, m), 3.91 (2H, s), 3.96 (2H, t), 4.29 (2H, t), 6.87–6.98 (4H, m), 7.06–7.15 (8H, m) | C₃₀H₃₄ClFN₂O₂ (hydrochloride).1/3H₂O<br>    C   H   N<br>Calcd: 69.96 6.79 5.44<br>Found: 69.87 6.66 5.37 |

TABLE I-continued

| | | | | |
|---|---|---|---|---|
| 59 | 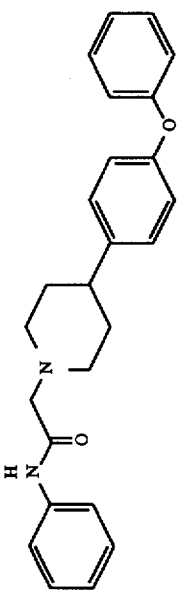 | Colorless crystals (hydrochloride) 205–206° C. (methanol/ ether) | (hydrochloride) 3043, 2491, 1695, 1599, 1553, 1508, 1489, 1446, 1237, 1171, 1088, 759 | 1.82 (2H, m), 1.93 (2H, m), 2.42 (2H, m), 2.56 (1H, tt), 3.05 (2H, m), 3.17 (2H, s), 6.98 (2H, d), 7.01 (2H, d), 7.25–7.38 (8H, m), 7.59 (2H, d) 9.19 (1H, brs) | $C_{25}H_{27}ClN_2O_2$ (hydrochloride)<br>　　C　　H　　N<br>Calcd: 70.99 6.43 6.62<br>Found: 70.93 6.44 6.60 |
| 60 | 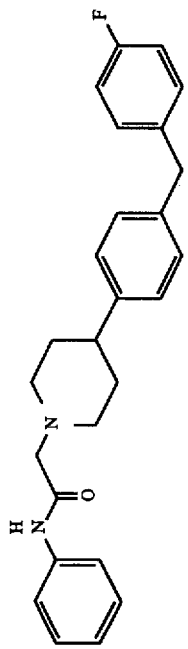 | Colorless crystals (hydrochloride) 187–188° C. (methanol/ ether) | (hydrochloride) 3230, 3058, 2504, 1690, 1600, 1555, 1508, 1445, 1315, 1224, 1157, 761 | 1.73–1.96 (4H, m), 2.40 (2H, m), 2.54 (1H, tt), 3.04 (2H, m) 3.16 (2H, s), 3.93 (2H, s) 6.95–7.38 (9H, m), 7.58 (2H, d), 9.18 (1H, brs) | $C_{24}H_{25}ClFN_2O$ (hydrochloride)<br>　　C　　H　　N<br>Calcd: 71.14 6.43 6.38<br>Found: 71.26 6.38 6.34 |
| 61 | 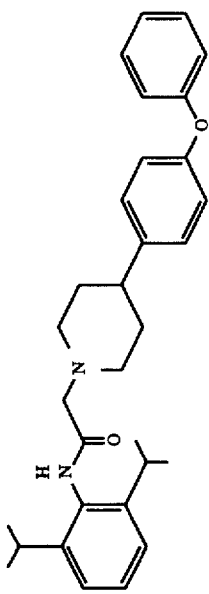 | Colorless crystals (hydrochloride) 140–141° C. (methanol/ ether) | (hydrochloride) 3484, 3159, 2961, 1687, 1590, 1530, 1507, 1488, 1396, 1237, 1167, 870 | 1.25 (12H, d), 1.84 (2H, m), 1.98 (2H, m), 2.51 (2H, m), 2.60 (1H, tt), 3.08 (2H, q), 3.18 (2H, m), 3.27 (2H, s), 6.99 (2H, d), 7.03 (2H, d), 7.11 (1H, t), 7.18–7.37 (7H, m), 8.47 (1H, brs) | — |

TABLE I-continued

| | | | | |
|---|---|---|---|---|
| 62 | 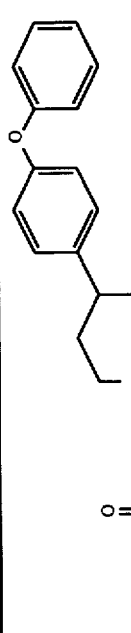 | Colorless crystals (hydrochloride) 218–220° C. (methanol/ ether) | (hydrochloride) 3444, 3312, 2928, 2667, 1651, 1590, 1543, 1511, 1490, 1305, 1240, 1072 | 1.67–1.95 (4H, m), 2.18 (2H, m), 2.53 (1H, tt), 2.65 (2H, t), 3.07 (2H, m), 3.58 (2H, dt), 6.86 (1H, brs), 6.95 (2H, d), 6.99 (2H, d), 7.08 (1H, t), 7.19 (2H, d), 7.32 (2H, t), 7.42–7.53 (3H, m), 7.79 (2H, d) | $C_{26}H_{27}ClN_2O_2$ (hydrochloride)<br>    C    H    N<br>Calcd: 71.46 6.69 6.41<br>Found: 71.61 6.65 6.41 |
| 63 | 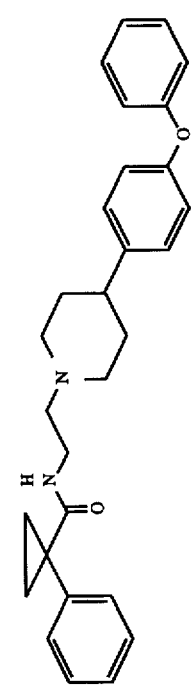 | Colorless crystals (hydrochloride) 130–131° C. (methanol/ ether) | (hydrochloride) 3398, 2934, 1648, 1589, 1536, 1508, 1489, 1238, 1074, 871, 853, 751 | 1.03 (2H, dd), 1.33 (2H, m), 1.60 (2H, dd), 1.67 (2H, m), 1.99 (2H, m), 2.35 (2H, t), 2.38 (1H, tt), 2.73 (2H, m), 3.24 (2H, dt), 6.13 (1H, brs), 6.97 (2H, d), 7.01 (2H, d), 7.09 (1H, t) 7.12 (2H, d), 7.28–7.47 (7H, m) | — |
| 64 | 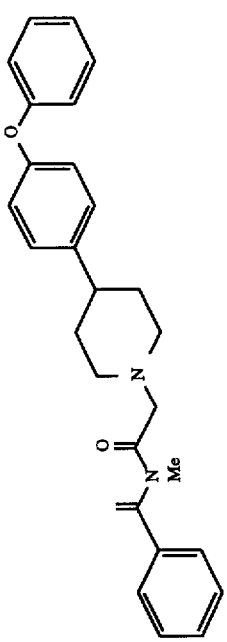 | Colorless crystals (fumarate) 79–80° C. (methanol/ ether) | (fumarate) 3401, 2932, 1670, 1633, 1589, 1508, 1490, 1372, 1240, 1171, 984, 778 | 1.75 (4H, m), 2.21 (2H, m), 2.42 (1H, m), 3.02 (2H, m), 3.15 (3H, s), 3.24 (2H, s) 5.27 (1H, s), 5.72 (1H, s), 6.94 (2H, d), 7.01 (2H, d), 7.10 (1H, t), 7.13 (2H, d), 7.28–7.50 (7H, m) | — |

The anti-veratridine effect of the above synthesized compounds, the T-type Ca$^{2+}$ channel inhibitory effect, and the dopamine D$_2$ receptor blocking effect were evaluated by the following methods. The results are shown in Table II, Table III, and Table IV.

Veratridine-induced Sodium Channel Activity Inhibitory Effect

The membrane potential of the synaptosomes prepared from the brain membrane of Wistar rats (male, 10 to 12 weeks old) was measured by the method of Aiuchi et al. [T. Aiuchi et al: Biochimi. Biophys. Acta. 771, 228 (1984)] using a membrane potential sensitive fluorescent dye Rhodamine 6G to evaluate the effects of suppression of the compound on the veratridine-induced depolarization response. The results are shown in Table II.

TABLE II

| Compound no. | Anti-veratridine effect (inhibiting rate %) (compound 0.1 μM) |
|---|---|
| 29 | 27.9 |
| 30 | 21.4 |
| 32 | 35.7 |
| 33 | 37.5 |
| 34 | 50.2 |
| 35 | 40.6 |
| 36 | 55.1 |
| 37 | 62 |
| 38 | 56.6 |
| 39 | 16.6 |
| 41 | 30.4 |
| 42 | 16.6 |
| 47 | 17.3 |
| 49 | 17 |
| 53 | 33.8 |
| 54 | 29.4 |
| 56 | 38.4 |
| 57 | 32.8 |
| 59 | 32.9 |
| 60 | 33.9 |
| 62 | 36 |
| 63 | 36.2 |
| 64 | 31.5 |

T-Type Calcium Channel Inhibitory Effect

The hippocampal CA1 pyramidal cells were isolated from Wistar rats (male/female, 1 week old) in accordance with the method of Takahashi et al. [K. Takahashi et al.; J. Pharmacol. Exp. Ther., 256, 169 (1991)] and the T-type calcium current under conditions of a fixed membrane potential was measured using the whole-cell configuration of the pach clamp technique. The effects of the compounds were evaluated from the rate of suppression of the peak current after one minute of application using the concentration clamp method. The results are shown in Table III.

TABLE III

| Compound no. | T-type Ca$^{2+}$ channel inhibitory effect IC$_{50}$ (μM) |
|---|---|
| 34 | 10 |
| 53 | 2.8 |
| 57 | 1.5 |

Dopamine D$_2$ Receptor Blocking Effect

57 μl of the membrane fraction prepared from the striatum of Wister male rats (6 weeks old) was incubated in a buffer at 25° C. for one hour along with the compound and 1.0 nM [$^3$H] raclopride. A GF/C glass filter (0.1% polyethylene imine treatment) was used for separation of B/F, then the radioactivity was measured by a beta plate and the effect of the compound was evaluated. The results are shown in Table IV.

TABLE IV

| Compound no. | Dopamine D$_2$ receptor blocking effect IC$_{50}$ (nM) |
|---|---|
| 32 | >1000 |
| 34 | 7000 |
| 36 | >1000 |
| 37 | >1000 |
| 53 | 1260 |
| Flunarizine | 228 |

INDUSTRIAL APPLICABILITY

According to the present invention, it is possible to obtain novel arylpiperidine and arylpiperazine derivatives and their salts useful as medicaments for the alleviation or treatment of symptoms due to ischemic diseases and symptoms derived from seizures, epilepsy, and migraine which have a powerful action in suppressing cytotoxic Ca$^{2+}$ overload and which are free from side effects.

We claim:

1. A compound having the general formula (I) or its salt:

$$\begin{array}{c} R^1 \\ \diagdown \\ N-(A)_m-(CH_2)_n- \\ \diagup \\ R_2-(B)_p \end{array}$$

[piperidine ring]—N Z—[phenyl ring with E]—X—[phenyl ring]—Y wherein, A and B represent a carbonyl group or a sulfonyl group, m and p are different and represent 0 or 1, R$^1$ and R$^2$ may be the same or different from each other and represent a hydrogen atom, an unsubstituted or substituted alkyl group, an unsubstituted or substituted aryl group, an unsubstituted or substituted aralkyl group, unsubstituted or substituted heterocyclic group containing nitrogen, an unsubstituted or substituted heterocyclic group containing oxygen or R$^1$ and R$^2$, taken together with the nitrogen atom to which they are linked, may form an unsubstituted or substituted heterocyclic group, provided that when B is a sulfonyl group, R$^2$ does not represent a hydrogen atom, n is an integer of 1 to 6, X represents a methylene group or an oxygen atom, E and Y may be the same or different from each other and represent a hydrogen atom, a halogen atom, an alkoxy group, or an alkyl group which may be substituted by a halogen atom, the dotted line shows the presence or absence of a bond, when said dotted line shows the present of a bond, Z represents a carbon atom, and when said dotted line shows the absence of a bond, Z represents CH or a nitrogen atom.

2. A compound or its salt as claimed in claim 1, wherein, in the general formula (I), Z represents CH or a nitrogen atom.

3. A compound or its salt as claimed in claim 1, wherein, in the general formula (I), X represents a methylene group.

4. A compound or its salt as claimed in claim 1, wherein, in the general formula (I), X represents an oxygen atom.

5. A compound or its salt as claimed in claim 1, wherein one of the substituents $R^1$ and $R^2$ in the general formula (I) represents a hydrogen atom.

6. A compound or its salt as claimed in claim 5, wherein one of the substituents $R^1$ and $R^2$ in the general formula (I) represents a hydrogen atom and the other represents an unsubstituted or substituted aralkyl group.

7. A compound or its salt as claimed in claim 5, wherein one of the substituents $R^1$ and $R^2$ in the general formula (I) represents a hydrogen atom and the other represents an unsubstituted or substituted aryl group.

8. A compound or its salt as claims in claim 1, wherein the substituents $R^1$ and $R^2$ in the general formula (I), taken together with the nitrogen atom to which they are linked, form an unsubstituted or substituted heterocyclic group.

9. A pharmaceutical composition comprising the compound having the general formula (I) according to claim 1 or its pharmaceutically acceptable salt, in a pharmaceutically effective amount, and a pharmaceutically acceptable carrier therefor.

10. A pharmaceutical composition for the alleviation or treatment of symptoms due to ischemic diseases comprising the compound having the general formula (I) according to claim 1 or its pharmaceutically acceptable salt, in an amount effective for the alleviation or treatment of symptoms due to ischemic diseases, and a pharmaceutically acceptable carrier therefor.

11. A pharmaceutical composition for suppression of $Ca^{2+}$ overload comprising the compound having the general formula (I) according to claim 1 or it pharmaceutically acceptable salt, in an amount effective to suppress $Ca^{2+}$ overload, and a pharmaceutically acceptable carrier therefor.

12. A method of alleviating or treating symptoms due to ischemic diseases in a patient comprising administering to the patient a compound according to claim 1 in an amount effective to alleviate or treat symptoms due to ischemic diseases.

13. A method of suppressing $Ca^{2+}$ overload in a patient comprising administering to said patient a compound according to claim 1 in an amount effective to suppress $Ca^{2+}$ overload.

* * * * *

UNITED STATES PATENT AND TRADEMARK OFFICE
CERTIFICATE OF CORRECTION

PATENT NO. : 5,723,475
DATED : Mar. 3, 1998
INVENTOR(S) : Hirokazu ANNOURA ET AL.

It is certified that error appears in the above-identified patent and that said Letters Patent is hereby corrected as shown below:

On the cover page:

Item No. [87], please change "PCT Pub. Date: June 9, 1996" to --PCT Pub. Date: Sept. 6, 1996--.

Claim 1, line 51, after "atom," please insert --and further wherein $R^1$ and $R^2$, taken together with the nitrogen atom to which they are linked, form an unsubstituted or substituted heterocyclic group, m is 1,--.

Signed and Sealed this

First Day of September, 1998

*Attest:*

*Attesting Officer*

BRUCE LEHMAN

Commissioner of Patents and Trademarks